(12) United States Patent
Wang et al.

(10) Patent No.: US 6,517,992 B1
(45) Date of Patent: Feb. 11, 2003

(54) N-SULFONYLOXYIMIDE COMPOUND AND RADIATION-SENSITIVE RESIN COMPOSITION USING THE SAME

(75) Inventors: Yong Wang; Eiichi Kobayashi; Masaaki Miyaji; Jun Numata, all of Yokkaichi; Tsutomu Shimokawa, Suzuka, all of (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 09/707,939

(22) Filed: Nov. 8, 2000

(30) Foreign Application Priority Data

Nov. 9, 1999 (JP) .......................... 11-317652

(51) Int. Cl.$^7$ ...................... G03F 7/004; C07D 207/46
(52) U.S. Cl. ..................... 430/270.1; 430/920; 548/542
(58) Field of Search ............................ 430/270.1, 920; 522/28, 50; 548/542

(56) References Cited

U.S. PATENT DOCUMENTS

| | | | | |
|---|---|---|---|---|
| 5,965,748 A | * | 10/1999 | Kamabuchi et al. | 548/542 |
| 5,981,140 A | * | 11/1999 | Sato et al. | 430/270.1 |
| 6,165,674 A | * | 12/2000 | Taylor et al. | 430/270.1 |

FOREIGN PATENT DOCUMENTS

EP          0959389          11/1999

OTHER PUBLICATIONS

Patents Abstracts of Japan, vol. 1996, No. 11, Nov. 29, 1996 & JP 08 184965 A (Jul. 16, 1996) *abstract*.
Patent Abstracts of Japan, vol. 2000, No. 01, Jan. 31, 2000 & JP 11 297597 A (Oct. 29, 1999) *abstract*.
Patent Abstracts of Japan, vol. 1996, No. 11, Nov. 29, 1996 & JP 08 179508 A (Jul. 12, 1996) *abstract*.

* cited by examiner

*Primary Examiner*—Rosemary Ashton
(74) *Attorney, Agent, or Firm*—Piper Rudnick, LLP; Steven B. Kelber

(57) ABSTRACT

An N-sulfonyloxyimide compound having the formula (1):

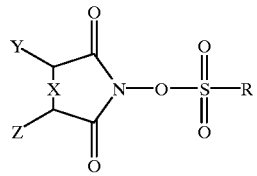

(1)

wherein X represents a single bond or a double bond, Y and Z represent a hydrogen atom or others and may combine to form a cyclic structure; and R is a group having the formula (2):

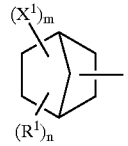

(2)

wherein $X^1$ represents an organic group having an ester linkage, $R^1$ represents an alkyl group or an alkoxyl group; and m is an integer of 1 to 11 and n is an integer of 0 to 10, satisfying $m+n \leq 11$; and chemically amplified positive and negative radiation-sensitive resin compositions using the compound are provided. The N-sulfonyloxyimide compound is a good radiation-sensitive acid-generating agent, has no problem of volatilization or side reaction, can keep dark reaction from taking place during the storage. The compound is useful as a component of radiation-sensitive chemically amplified resists.

21 Claims, 6 Drawing Sheets

N-SULFONYLOXYIMIDE COMPOUND AND RADIATION-SENSITIVE RESIN COMPOSITION USING THE SAME

BACKGROUND OF THE INVENTION

1. Field of the Invention

This invention relates to a novel N-sulfonyloxyimide compound suitable as a radiation-sensitive acid-generating agent component of radiation-sensitive resin compositions used as chemically amplified resists suited for fine processing made by various radiations such as ultraviolet radiations, far-ultraviolet radiations, X-raditions and charged particles. It also relates to chemically amplified positive and negative radiation-sensitive resin compositions making use of such an N-sulfonyloxyimide compound.

2. Description of the Prior Art

In the field of fine processing as typified by the fabrication of integrated-circuit devices, the size of processing in lithography is being made finer in order to achieve a higher degree of integration. In recent years, lithographic processes that enables stable fine processing in a size of 0.5 μm or finer is powerfully being developed.

However, in conventional processes making use of visible radiations (wavelength: 400 to 700 nm) or near ultraviolet radiations (300 to 400 nm), it is difficult to form such fine patterns in a high precision. Accordingly, proposed are lithographic processes that can achieve a wider focal depth and make use of radiations having a short wavelength (wavelength: 300 nm or shorter) effective for making design rules finer.

Radiations having such a short wavelength may include, e.g., far-ultraviolet radiations of KrF excimer lasers (wavelength: 248 nm) or ArF excimer lasers (wavelength: 193 nm), X-radiations such as synchrotron radiations, and charged-particle radiations such as electron radiations. Then, as a high-resolution resist adaptable to these short-wavelength radiations, "chemically amplified resist resist" is proposed by International Business Machine (IBM) Corp. At present, improvements of this chemically amplified resist are being energetically made.

Chemically amplified resists are resists with which a resist pattern is formed by generating an acid by irradiation with radiations (hereinafter "exposure") to a radiation-sensitive acid-generating agent contained therein to cause a chemical change (e.g., change in polarity, destruction of chemical bonds, or cross-linking reaction) in resist film by the catalytic action of this acid and utilize a phenomenon that the solubility to a developing solution changes at the exposed areas.

In such chemically amplified resists, the radiation-sensitive acid-generating agent is known to have a great influence on the function as a resist, and is commonly grouped into an ionic one and a nonionic one. Radiation-sensitive acid-generating agents comprised of N-sulfonyloxyimides, which are nonionic, have a good solubility in non-polar or medium-polar solvents which are widely used in resists, and products formed after exposure are well soluble in water-based alkaline developing solutions. Radiation-sensitive acid-generating agents for chemically amplified resists are widely used in the form of a single agent or a mixture with other photo-acid-generating agent.

Now, N-sulfonyloxyimides are grouped into the following three types by the types of sulfonic acids corresponding thereto.

Sulfonyloxyimides generated from superacids (3-1) & (3-2):

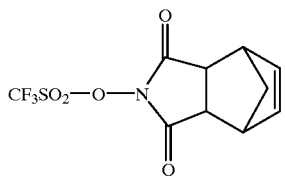

(3-1)

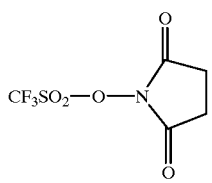

(3-2)

Sulfonyloxyimides generated from aromatic sulfonic acids (3-3) & (3-4):

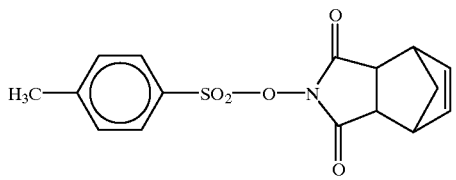

(3-3)

(3-4)

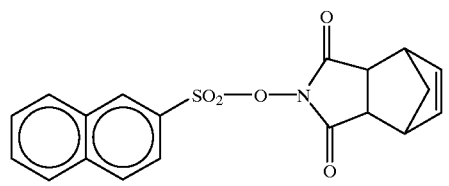

Sulfonyloxyimides generated from aliphatic sulfonic acids (3-5) & (3-6):

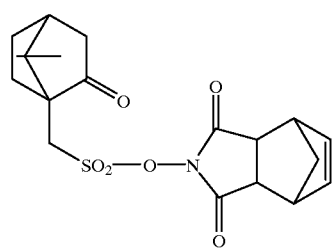

(3-5)

(3-6)

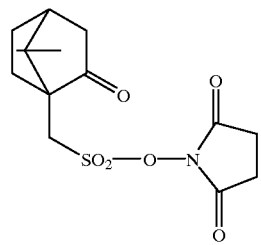

It, however, does not follow that these N-sulfonyloxyimides can satisfy all performances required in chemically amplified resists. More specifically, sulfonyloxyimides generated from superacids are fluorine-substituted and hence the acid generated has so low a boiling point as to have a possibility that the acid volatilizes at the time of baking to corrode an exposure assembly, and also has so high a chemical activity as to make it difficult to control side reaction at the time of protective group elimination reaction and cross-linking reaction. They have such disadvantages or besides, since they are esters of superacids, have a poor stability. Also, the sulfonyloxyimides generated from aromatic sulfonic acids have is disadvantages that they show so great a absorption in the wavelength region of far-ultraviolet radiations as to tend to cause a lowering of resolution performance.

On the other hand, the sulfonyloxyimides generated from aliphatic sulfonic acids have a relatively high transparency to far-ultraviolet radiations and the acid generated has an appropriate strength to enable relatively easy control of side reaction. Hence, they are especially useful among N-sulfonyloxyimide type radiation-sensitive acid-generating agents, as a component that compensates their disadvantages when used alone or in the form of a mixture with other radiation-sensitive acid-generating agent(s).

However, known aliphatic sulfonic acids, in particular, commercially readily available aliphatic sulfonic acids are limited, and hence no energetic studies have ever been made on the aliphatic sulfonyloxyimides. As an exception, N-sulfonyloxyimide compounds of a long-chain alkylsulfonic acid type and of a camphor sulfonic acid type are available. These compounds, however, have the following disadvantages. That is, the long-chain alkylsulfonic acid type sulfonyloxyimide compound greatly differs in polarity between sulfonyloxyimide moiety and long-chain alkyl moiety. Hence, it acts like a surface-active agent and, when added in a usual quantity as the radiation-sensitive acid-generating agent, microscopic air bubbles may be formed in the resist to bring about a possibility of greatly causing faulty coating or faulty development (or development defects). As for the camphor sulfonic acid type sulfonyloxyimide compound, it does not have such a problem, but a problem on stability remains unsettled. Since N-sulfonyloxyimide compounds are highly reactive sulfonyl esters, nucleophilic substitution reaction tends to take place. They may react with nucleophilic groups of other components in the resin, as exemplified by phenolic hydroxyl groups in a resin component and hydroxyl groups in a solvent component, or with water or the like remaining in a trace quantity in the resist, to become decomposed to cause a change in performance such as sensitivity of the resist. Even the camphor sulfonic acid type N-sulfonyloxyimide compound has such a disadvantage.

Accordingly, it has been earnestly sought to bring forth an N-sulfonyloxyimide compound which has a structure suited for commercial-scale manufacture, has no problem of volatilization or side reaction, can keep dark reaction from taking place during the storage of resist solutions and also is suitable as a radiation-sensitive acid-generating agent component of chemically amplified resists having a high resolution suited for fine processing.

SUMMARY OF THE INVENTION

Taking account of the above circumstances in the prior art, an object of the present invention is to provide a novel N-sulfonyloxyimide compound which has a structure suited for commercial-scale manufacture, especially can generate an acid in a good efficiency as having a high sensitivity (low exposure energy quantity) to far-ultraviolet radiations and charged-particle radiations, has no problem of volatilization or side reaction, can keep dark reaction from taking place during the storage of resist solutions and also is suitable as a radiation-sensitive acid-generating agent component of radiation-sensitive resin compositions used as chemically amplified resists having a high resolution suited for fine processing.

Another object of the present invention is to provide superior chemically amplified positive and negative radiation-sensitive resin compositions making use of such an N-sulfonyloxyimide compound.

According to the present invention, the above objects can firstly be achieved by an N-sulfonyloxyimide compound represented by the following general formula (1):

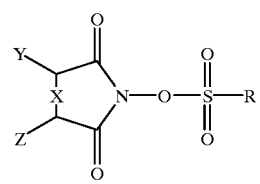

(1)

wherein in the general formula (1), X represents a single bond or a double bond, Y and Z each independently represent a hydrogen atom or a substituted or unsubstituted alkyl group having 1 to 10 carbon atoms, or Y and Z combine to form an alicyclic structure or heterocyclic structure; and R is a group represented by the following general formula (2):

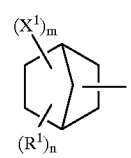

(2)

wherein in the general formula (2), $X^1$ represents an organic group having an ester linkage, having 2 to 10 carbon atoms, and, when $X^1$ is present in plurality, $X^1$'s may be the same with or different from each other; $R^1$ represents an alkyl group having 1 to 10 carbon atoms or an alkoxyl group having 1 to 10 carbon atoms, and, when $R^1$ is present in plurality, $R^1$'s may be the same with or different from each other; and m is an integer of 1 to 11 and n is an integer of 0 to 10, satisfying m+n $\leq$11.

(Hereinafter often "first invention").

According to the present invention, the above objects can secondly be achieved by a chemically amplified positive radiation-sensitive resin composition comprising (A) a radiation-sensitive acid-generating agent comprising the N-sulfonyloxyimide compound represented by the above general formula (1), and (B) an alkali-insoluble or alkali-slightly-soluble resin protected with an acid-cleavable group, the resin being capable of turning soluble in alkali upon cleavage of the acid-cleavable group (hereinafter often "second invention").

According to the present invention, the above objects can thirdly be achieved by a chemically amplified negative radiation-sensitive resin composition comprising (A) a radiation-sensitive acid-generating agent comprising the N-sulfonyloxyimide compound represented by the above general formula (1), (C) an alkali-soluble resin and (D) a compound capable of cross-linking the alkali-soluble resin in the presence of an acid (hereinafter often "third invention")

DESCRIPTION OF THE PREFERRED EMBODIMENTS

Figure 1:
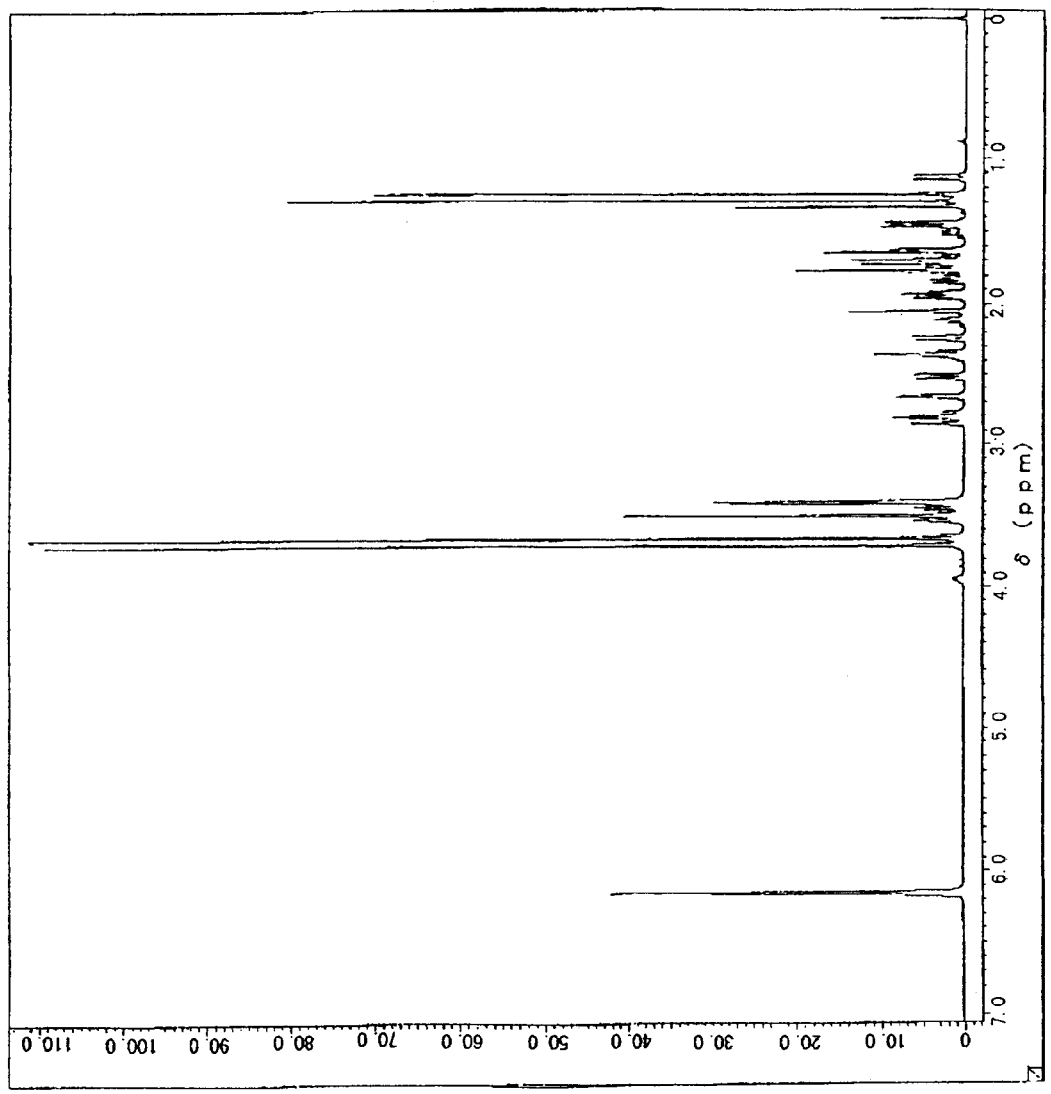
FIG. 1 is a graph showing the results of measurement by $^1$H-NMR analysis of an N-sulfonyloxyimide compound (PAG1) obtained in Synthesis Example 1.

The present invention will be described below in detail.

N-sulfonyloxyimide Compound

The present inventors repeated extensive studies in order to achieve the above objects. As the result, as exemplified by the following Reaction Scheme (4), they have used a substituted or unsubstituted ethylene (4a) [hereinafter "ethylene compound (4a)"] and a substituted or unsubstituted cyclopentadiene (4b) [hereinafter "cyclopentadiene compound (4b)"] (provided that at least one of the ethylene compound (4a) and the cyclopentadiene compound (4b) is a substituted compound) to synthesize an alicyclic olefin compound (4c) by the Diels-Alder reaction, followed by addition reaction of the alicyclic olefin compound (4c) with a bisulfite to obtain an alicyclic sulfonate (4d). Thereafter, as exemplified by the following Reaction Scheme (4), they have allowed this alicyclic sulfonate (4d) to react with thionyl chloride to synthesize a sulfonyl chloride (4e), further followed by reaction with an N-hydroxyimide (4f) to synthesize a novel N-sulfonyloxyimide compound represented by the above general formula (1).

[Reaction Scheme (4)]

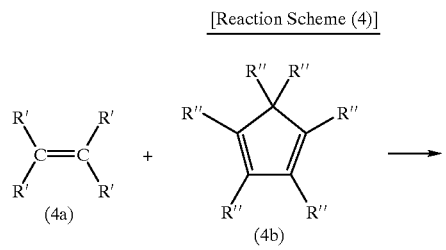

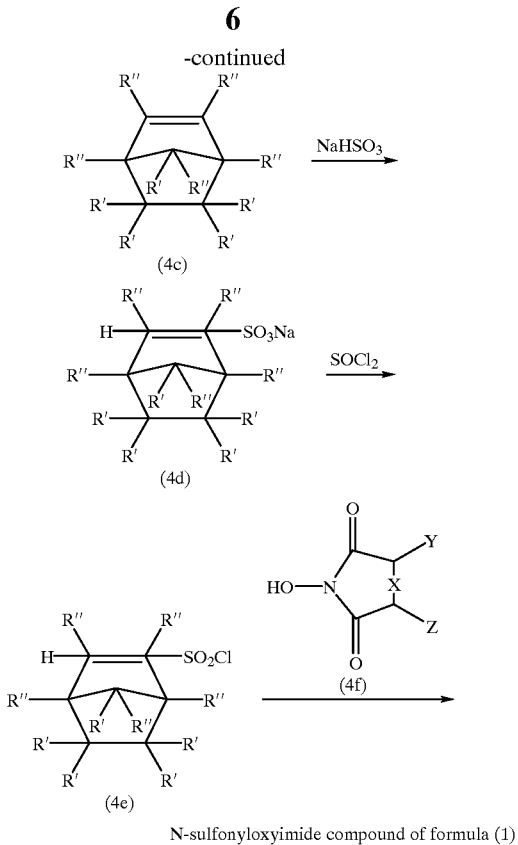

N-sulfonyloxyimide compound of formula (1)

In Reaction Scheme (4), R''s and R'''s each represent a hydrogen atom or the same group as $X^1$ or $R^1$ in the general formula (2); at least one of R''s and at least one of R'''s each represent the same group as $X^1$ in the general formula (2); and X, Y and Z are as defined in relation to the general formula (1).

With regard to the N-sulfonyloxyimide compound thus obtained, the present inventors made detailed studies on its properties and operation as a radiation-sensitive acid-generating agent for chemically amplified resists. As the result, they have found that such an N-sulfonyloxyimide comnpound can remarkably be kept from its dark reaction in the resist to promise a superior storage stability and can provide a high resolution suited for fine processing, especially can exhibit superior properties and operation in lithography making use of far-ultraviolet radiations or charged-particle radiations and is very suitable as a radiation-sensitive acid-generating agent component of radiation-sensitive resin compositions used as chemically amplified resists.

More specifically, the N-sulfonyloxyimide compound represented by the general formula (1) has a rigid cyclic structure and an ester linkage and also has an alkoxyl group in some cases. Hence, it has a good affinity for resin components in chemically amplified resists and has hydrophobicity and hydrophilicity in a well balanced state, and the acid generated can be low volatile. Also, since this N-sulfonyloxyimide compound is an ester of secondary sulfonic acid, the nucleophilic reaction may take place with greater difficulty than esters of primary sulfonic acid such as camphor sulfonic acid to have a superior storage stability. Moreover, this N-sulfonyloxyimide compound has good characteristics that it has a structure suited for commercial-scale manufacture, does not contain any elements which may adversely act on semiconductors and has no problem of volatilization or side reaction.

The N-sulfonyloxyimide compound that constitutes the first invention and is used as a radiation-sensitive acid-generating agent (hereinafter "acid-generating agent (A)") in the second invention radiation-sensitive resin composition and the third invention radiation-sensitive resin composition is detailed below.

In the general formula (1), X represents a single bond or a double bond, Y and Z each independently represent a hydrogen atom or a substituted or unsubstituted alkyl group having 1 to 10 carbon atoms, and Y and Z may combine to form an alicyclic structure or heterocyclic structure. As examples of the alicyclic structure and heterocyclic structure which may be formed here, they may include those represented by the following formulas [shown as the left-half moiety of the general formula (1)].

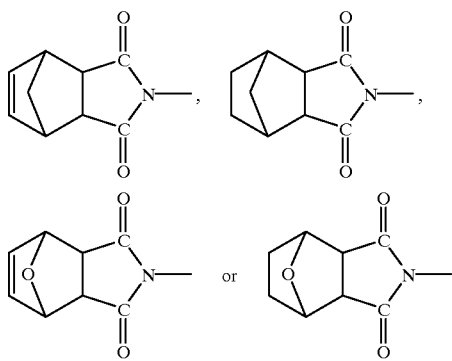

In the general formula (2), the organic group represented by $X^1$, having an ester linkage, may preferably include those represented by the following formulas (5-1) to (5-4). In particular, groups having 2 to 5 carbon atoms are preferred.

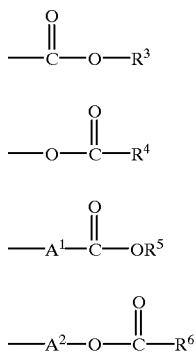

wherein in the formulas (5-1) to (5-4), $R^3$ to $R^6$ each represent an alkyl group having 1 to 6 carbon atoms, and preferably a methyl group, an ethyl group or an i-propyl group; and $A^1$ and $A^2$, each represent an alkylene group having I to 6 carbon atoms, and preferably a methylene group, an ethylene group, a 1,2-propylene group or a trimethylene group.

In the general formula (2), the alkyl group represented by $R^1$ may preferably be any of groups having 1 to 8 carbon atoms, such as a methyl group, an ethyl group, a n-propyl group, an i-propyl group, a n-butyl group, an i-butyl group, a sec-butyl group, a t-butyl group, a n-pentyl group, a n-hexyl group, a n-heptyl group, a n-octyl group and a cyclohexyl group. In particular, a methyl group, an ethyl group, an i-propyl group and a t-butyl group are preferred.

The alkoxyl group represented by $R^1$ may preferably be any of groups having 1 to 8 carbon atoms, such as a methoxyl group, an ethoxyl group, a n-propoxyl group, an i-propoxyl group, a n-butoxyl group, an i-butoxyl group, a sec-butoxyl group, a t-butoxyl group, a n-pentyloxyl group, a n-hexyloxyl group, a n-heptyloxyl group, a n-octyloxyl group and a cyclohexyloxyl group. In particular, a methoxyl group, an ethoxyl group, an i-propoxyl group and a t-butoxyl group are preferred.

In the general formula (2), m is an integer of 1 to 11, preferably an integer of 1 to 6, and particularly preferably an integer of 1 to 3.

In the general formula (2), n is an integer of 0 to 10, preferably an integer of 0 to 6, and particularly preferably an integer of 0 to 3.

As examples of the group represented by R in the N-sulfonyloxyimide compound, it may include compounds represented by the following formulas (6-1) to (6-20).

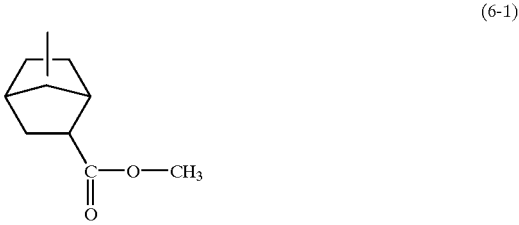

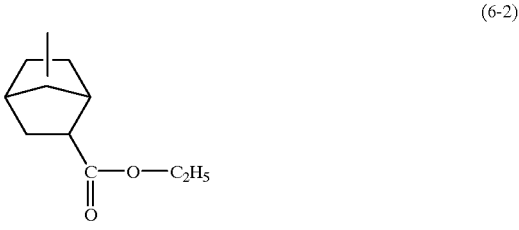

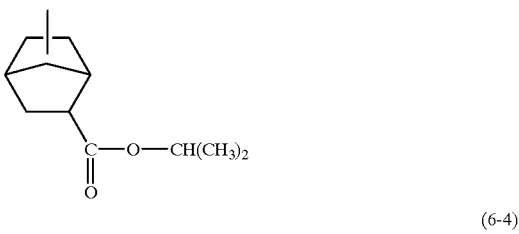

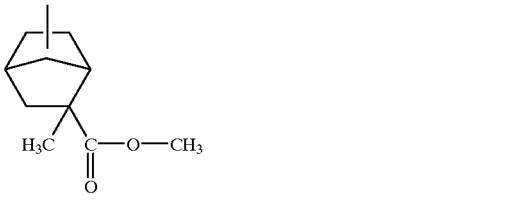

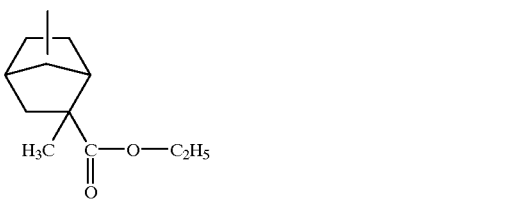

(6-6) 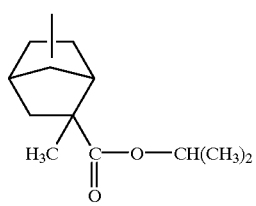
(6-7) 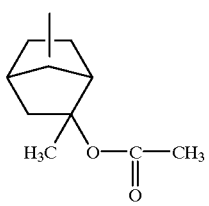
(6-8) 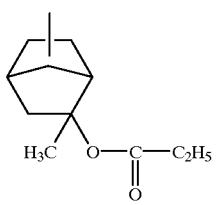
(6-9) 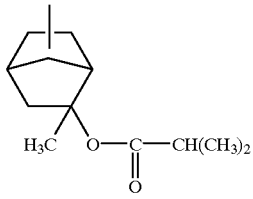
(6-10) 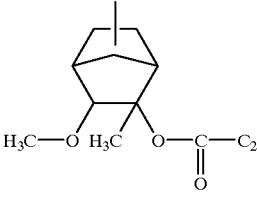
(6-11) 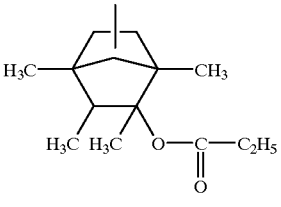
(6-12) 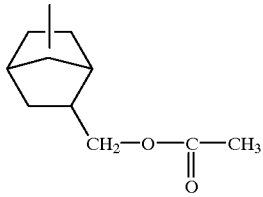
(6-13) 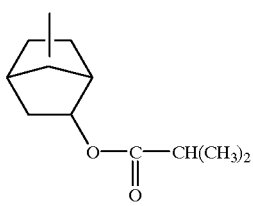
(6-14)
(6-15)
(6-16)
(6-17)
(6-18)
(6-19)

(6-20)
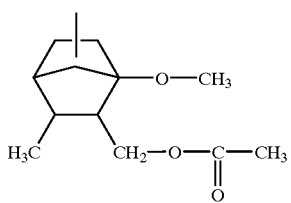
Then, as typical examples of the N-sulfonyloxyimide compound represented by the formula (1), it may include the following compounds.
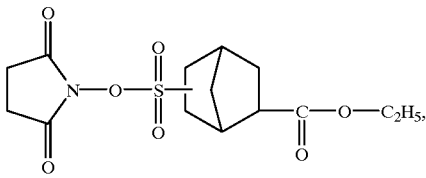
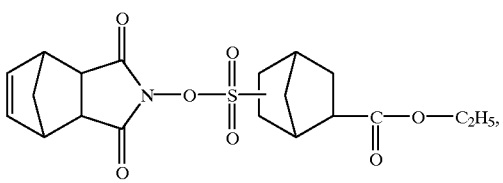
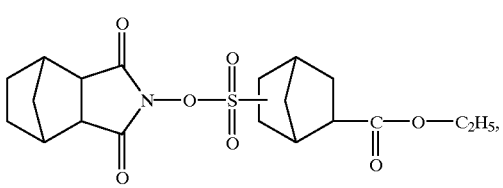
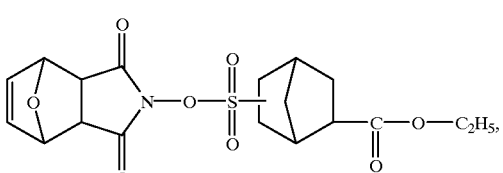
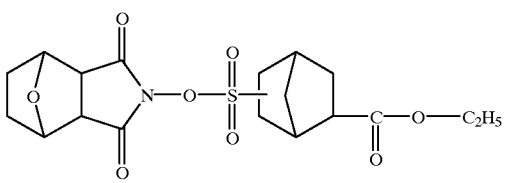
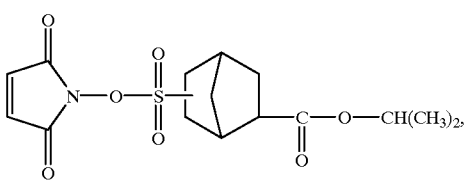
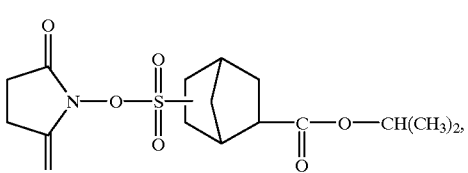
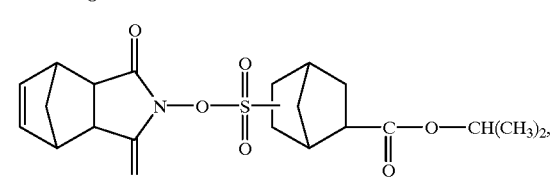
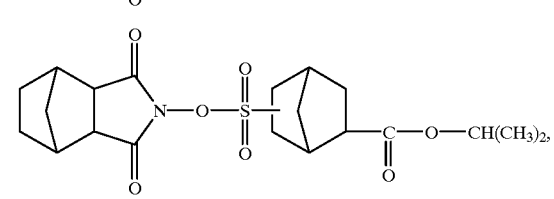

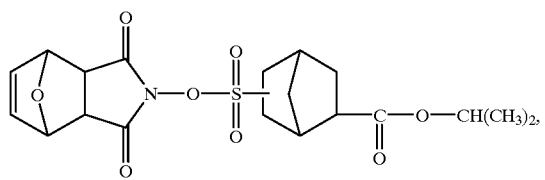
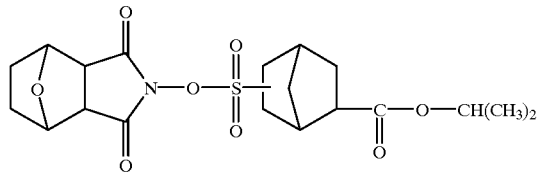
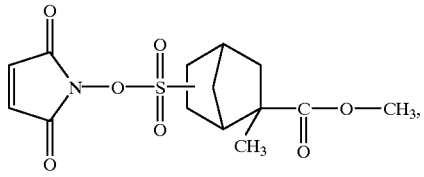
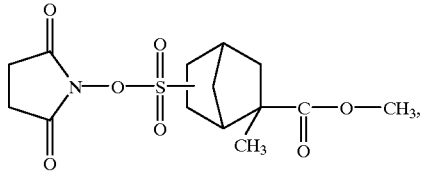
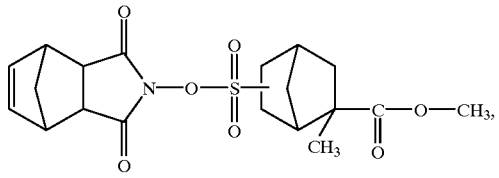
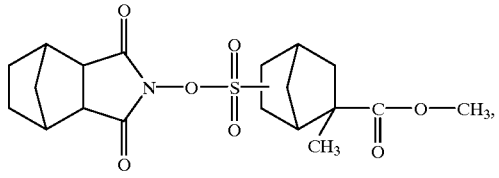
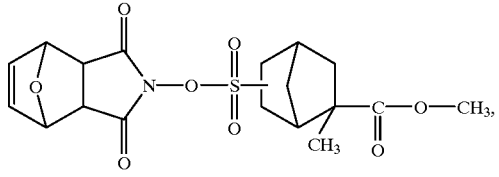
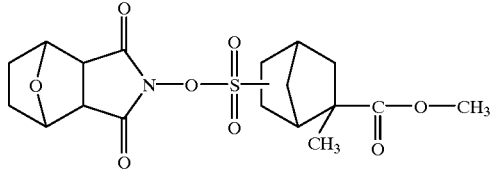
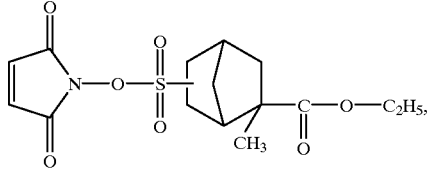
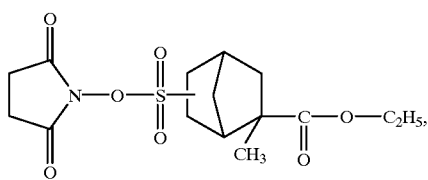
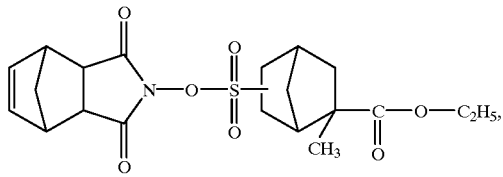
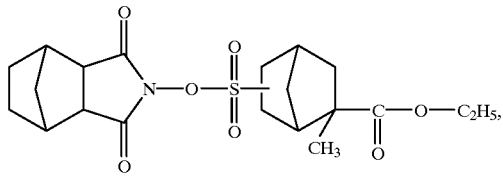
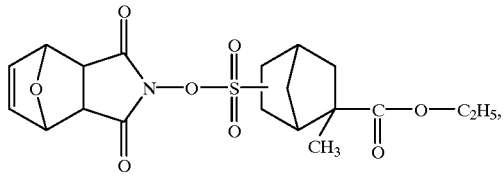
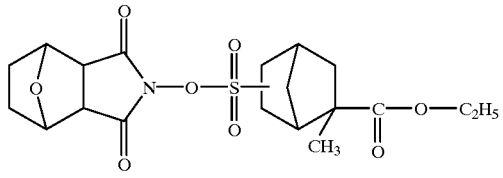
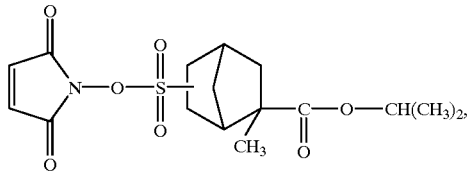
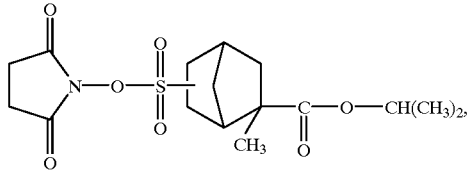
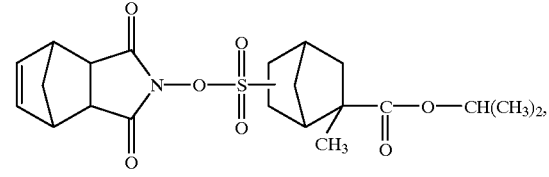
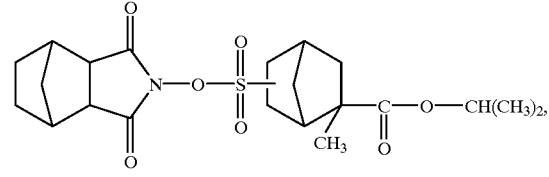

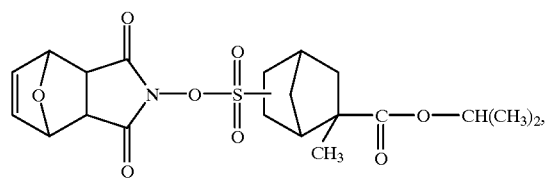
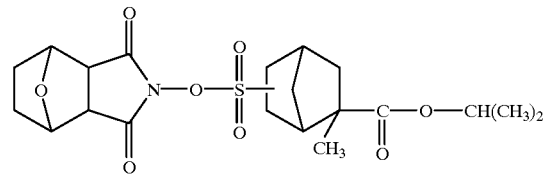
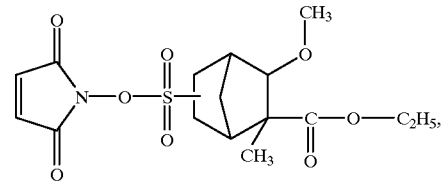
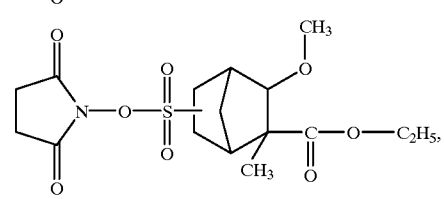
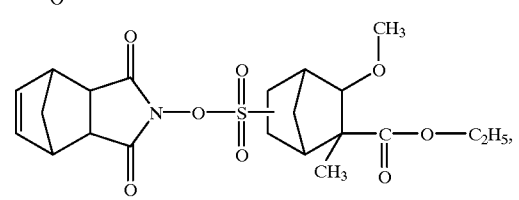
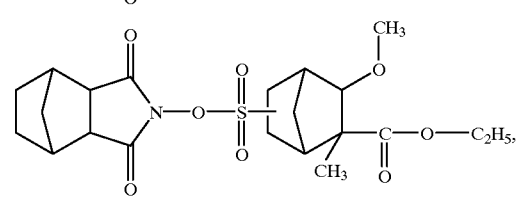
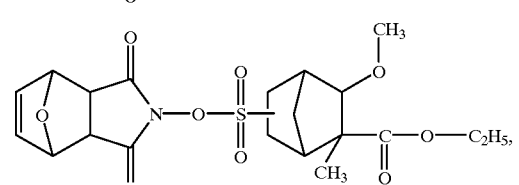
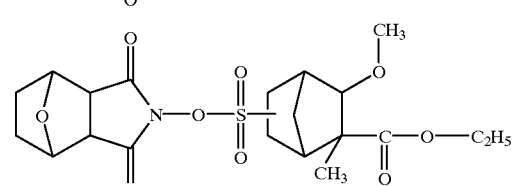
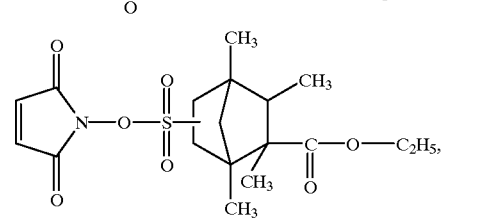
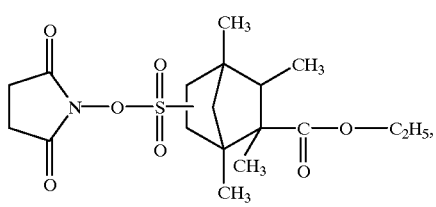
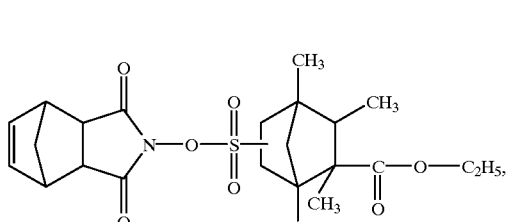
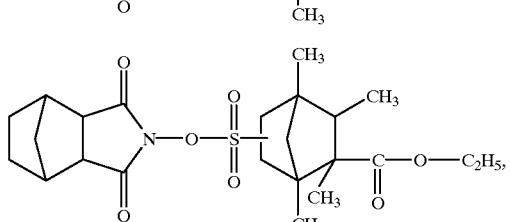
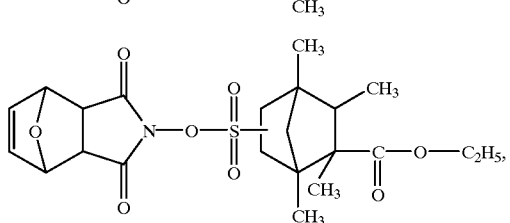
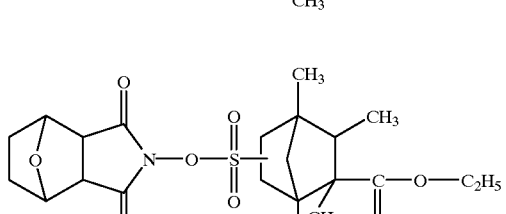
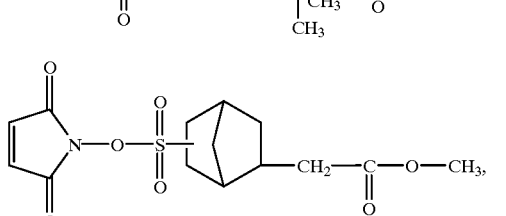
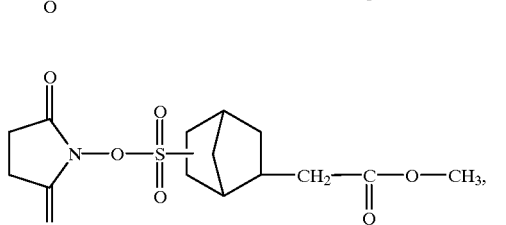
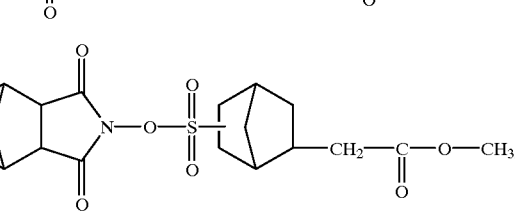

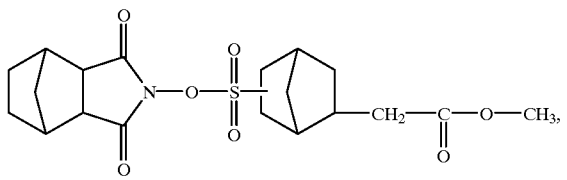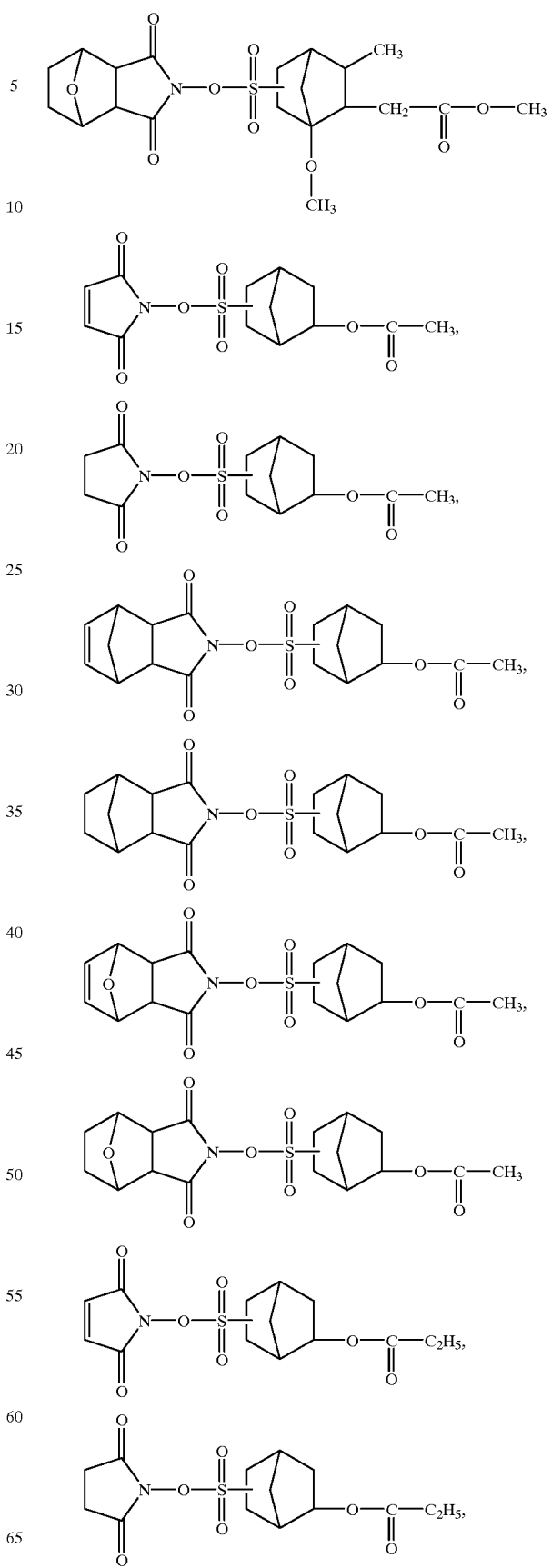

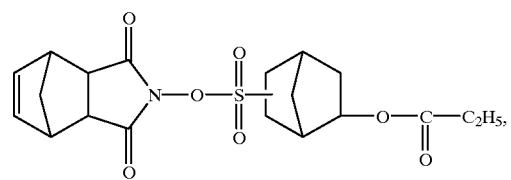
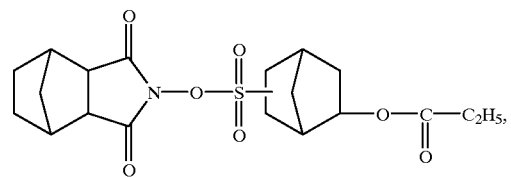
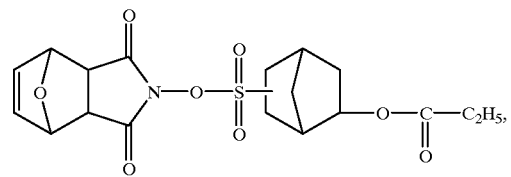
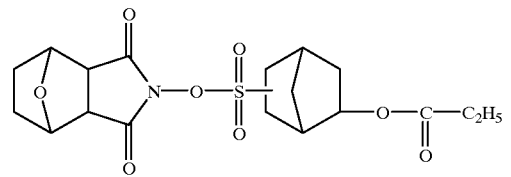
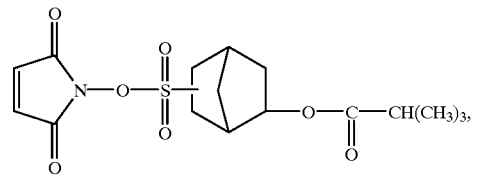
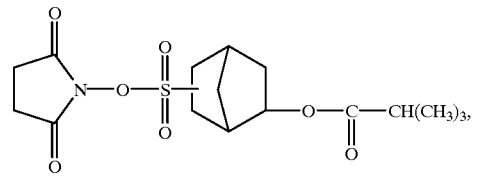
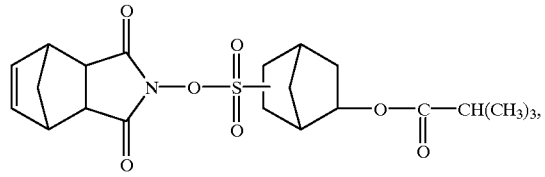
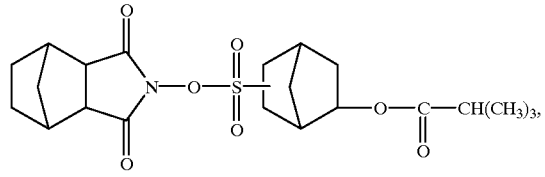
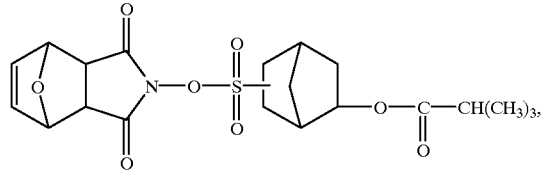
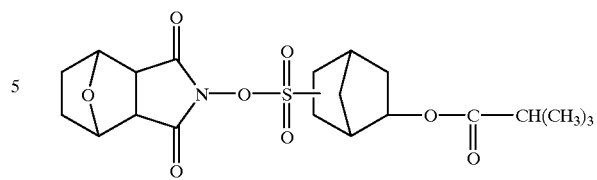
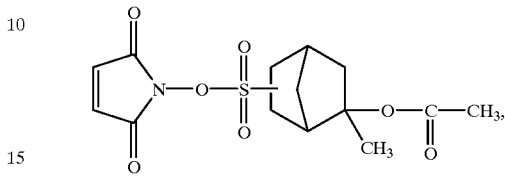
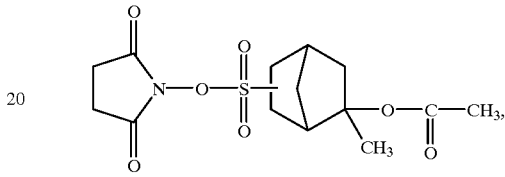
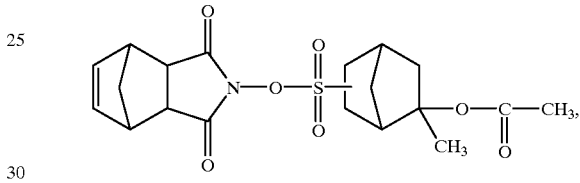
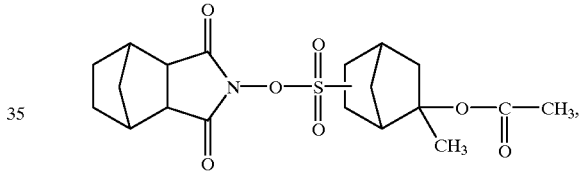
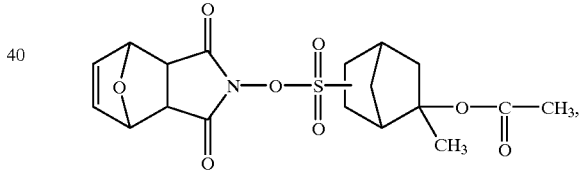
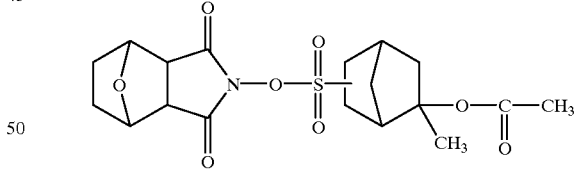
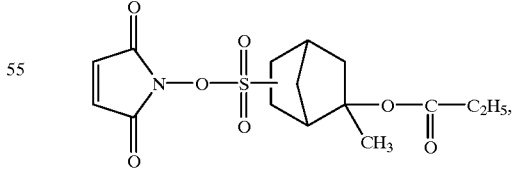
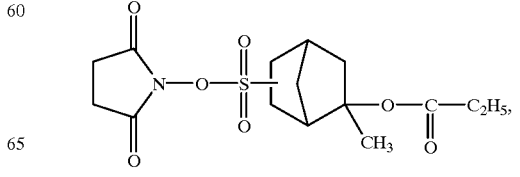

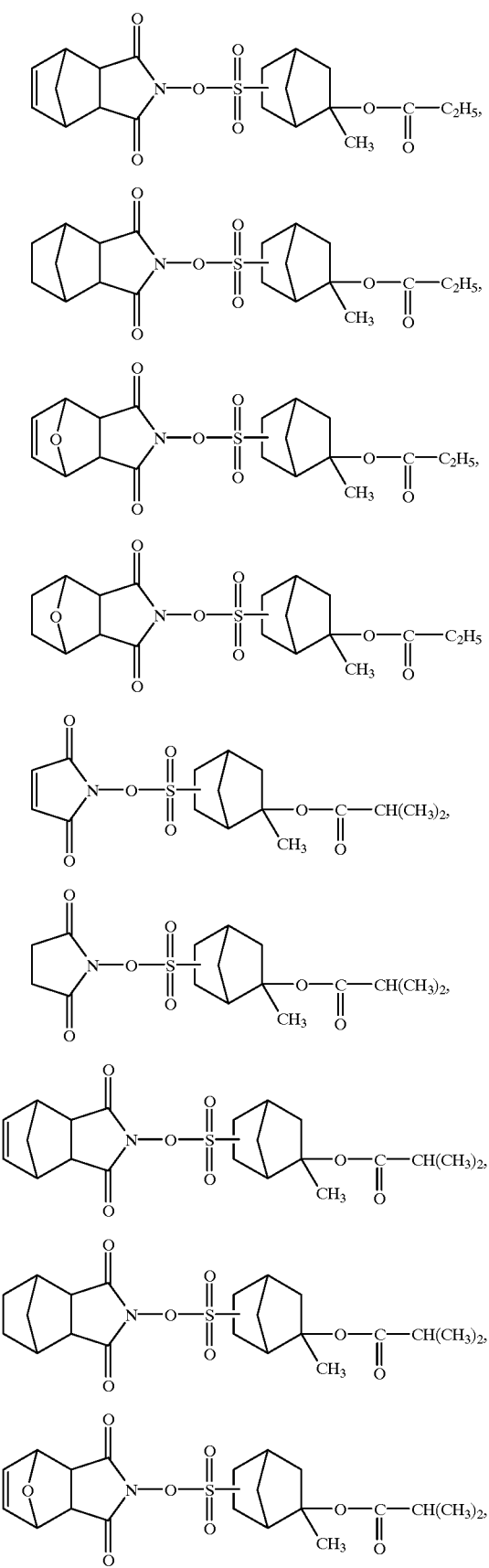
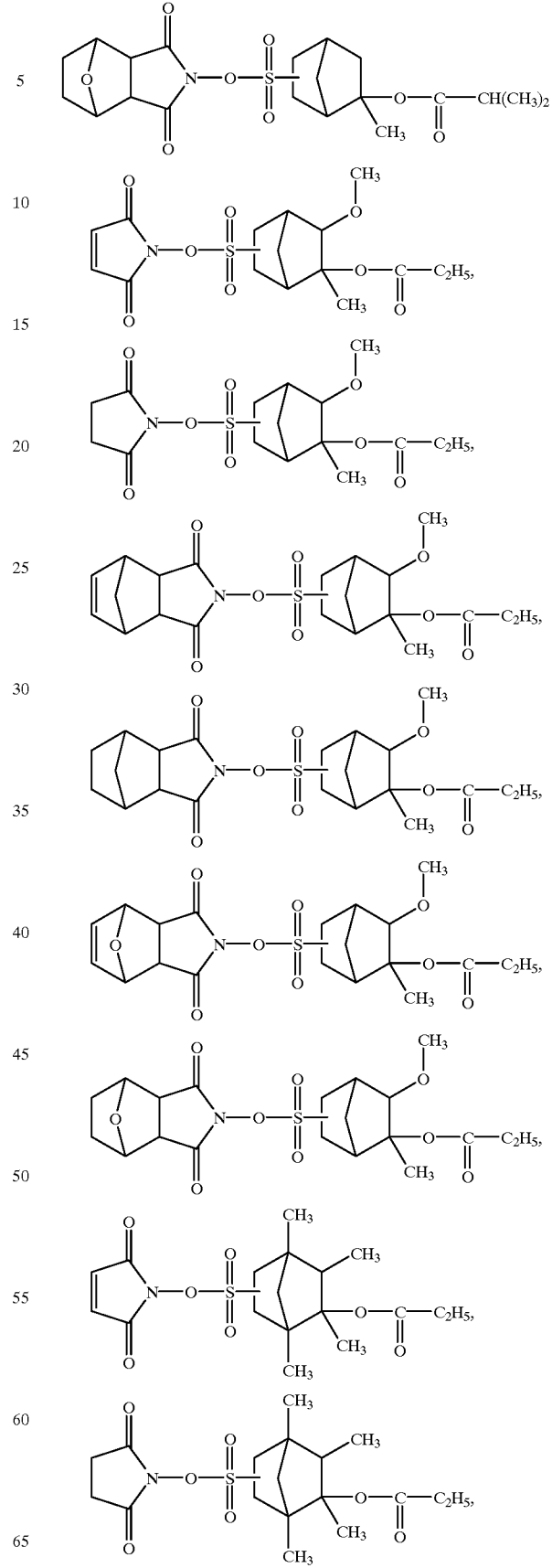

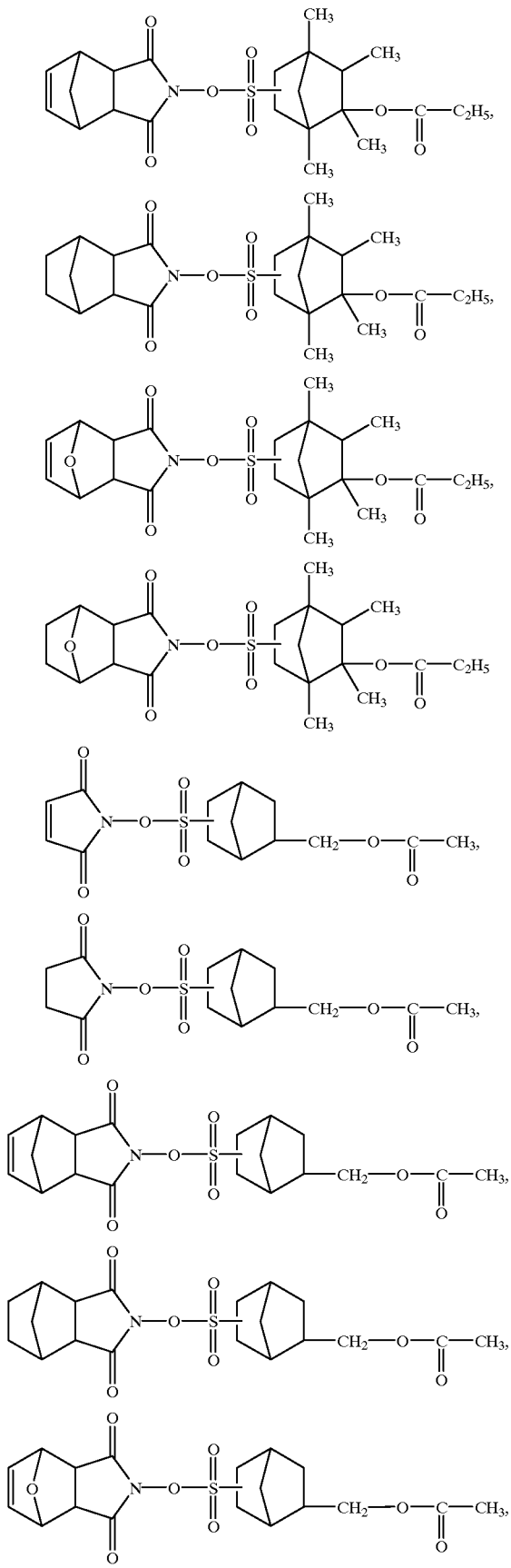
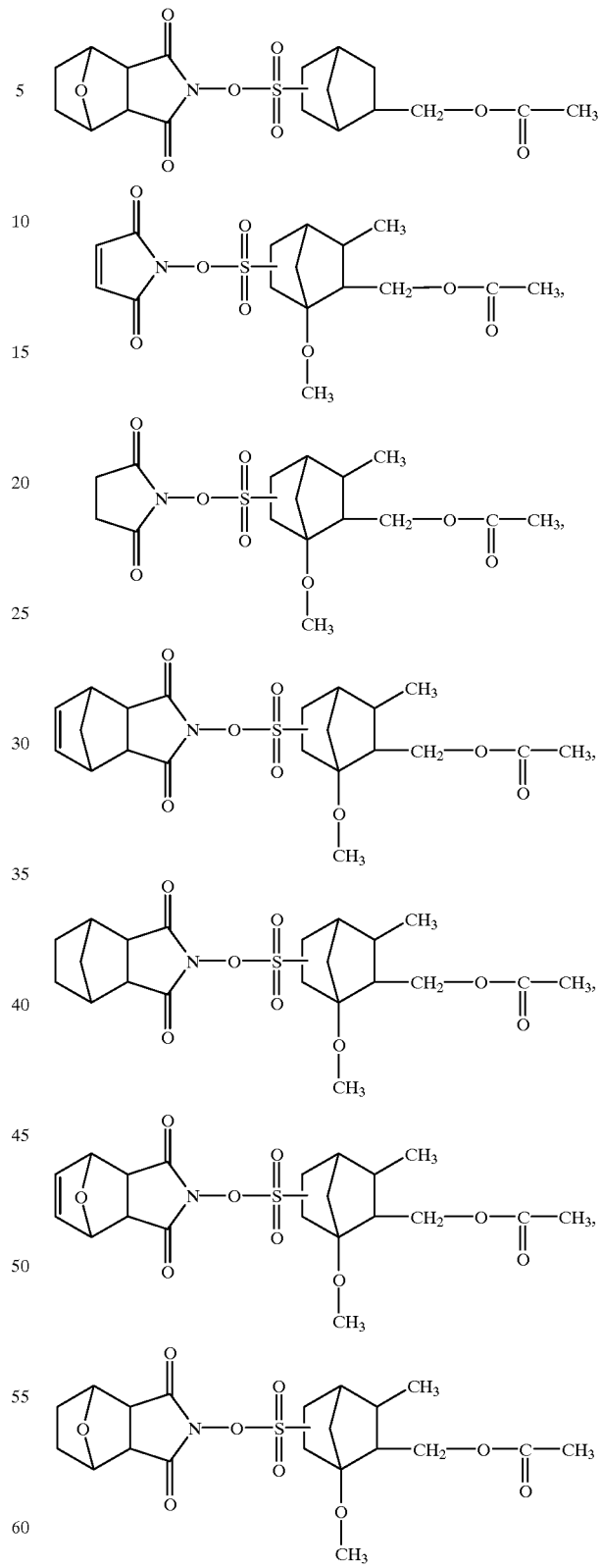
A process of synthesizing the N-sulfonyloxyimide compound represented by the general formula (1) is described below in a more specific manner, according to Reaction Scheme 4 set out previously.

First, the ethylene compound (4a) and the cyclopentadiene compound (4b) are subjected to the Diels-Alder reaction under heating to synthesize the alicyclic olefin compound (4c), followed by addition reaction of the alicyclic olefin compound (4c) with sodium bisulfite in a mixed solvent of an organic solvent and water to obtain a sodium alicyclic sulfonate (4d). Next, the sodium alicyclic sulfonate (4d) is allowed to react with thionyl chloride to synthesize a sulfonyl chloride (4e), and thereafter this is further allowed to react with the N-hydroxyimide (4f) to synthesize the novel N-sulfonyloxyimide compound (1).

In the above reaction, the Diels-Alder reaction of the ethylene compound (4a) with the cyclopentadiene compound (4b) may be carried out by a common method described in, e.g., "Comprehensive Organic Synthesis, B. M. Trose & I, Fleming, Bergamon Press, New York, 1991, Vol. V, p.315".

When this Diels-Alder reaction is carried out, the ethylene compound (4a) and the cyclopentadiene compound (4b) may usually be in a molar ratio of the former to the latter of from 0.01 to 100, and preferably from 0.1 to 10.

The reaction is carried out in the absence of a solvent or in a solvent such as toluene, xylene, N,N-dimethylformamide, tetrahydrofuran or 1,2-dichloroethane.

The reaction may usually be carried out at a temperature of from 20 to 250° C., and preferably from 80 to 180° C., and for a time of from 0.5 to 24 hours, and preferably from 4 to 12 hours. Where the reaction temperature is higher than the boiling points of reaction materials or solvents, a pressure vessel such as an autoclave may be used.

The addition reaction of the alicyclic olefin compound (4c) with sodium bisulfite may also be carried out according to a method described in, e.g., "K.H. Pfoertner, Helvetica Chimica Acta, 63 Fasc 3, 664, 1980".

In such addition reaction, a radical-generating agent such as 2,2'azobisisobutyronitrile (AIBN) may be added. This enables acceleration of the reaction and also improvement of yield, as so ascertained by the present inventors. The radical-generating agent may usually be used in an amount of from 0.01 to 10 parts by weight, and preferably from 0.5 to 5 parts by weight, based on 100 parts by weight of the sodium bisulfite.

The organic solvent used as a reaction solvent together with water may preferably be a solvent well compatible with water as exemplified by lower alcohols, tetrahydrofuran, N,N-dimethylformamide and acetonitrile, more preferably lower alcohols and N,N-dimethylformamide, and particularly preferably lower alcohols such as methanol, ethanol and i-propanol. The organic solvent may be used in such a proportion that it is usually from 5 to 100 parts by weight, preferably from 10 to 100 parts by weight, and more preferably from 20 to 90 parts by weight, based on 100 parts by weight of the total of the organic solvent and water.

The reaction may usually be carried out at a temperature of from 40 to 200° C., and preferably from 60 to 120° C., and for a time of from 0.5 to 72 hours, and preferably from 2 to 24 hours. Where the reaction temperature is higher than the boiling point of the organic solvent or water, a pressure vessel such as an autoclave may be used.

As for the reaction of the sodium alicyclic sulfonate (4d) with thionyl chloride, it may be carried out according to a method described in, e.g., Synthesis Example 1 given later. Also, the reaction of the sulfonyl chloride (4e) with the N-hydroxyimide (4f) may be carried out according to a method described in, e.g., Synthesis Example 1 given later.

As specific examples of the ethylene compound (4a) used in the above reaction, it may include methyl (meth)acrylate ["(meth)acrylate" is herein generically meant to be acrylate and methacrylate; the same applies hereinafter], methyl (meth)acrylate, ethyl (meth)acrylate, isopropyl (meth) acrylate, vinyl acetate, vinyl propionate, 1-methylvinyl butyrate, 1-methylvinyl acetate, 1-methylvinyl propionate, 1-methylvinyl butyrate, methyl 3-methoxy(meth)acrylate, ethyl 3-methoxy(meth)acrylate, n-propyl 3-methoxy(meth) acrylate and isopropyl 3-methyoxy(meth)acrylate.

As specific examples of the cyclopentadiene compound (4b), it may include cyclopentadiene, 1-methylcyclopentadiene, 1,4-dimethylcyclopentadiene, 1,4-dimethoxycyclopentadiene, 5-isopropylcyclopentadiene and 1,2,3,4-tetramethylcyclopentadiene.

As specific examples of the N-hydroxyimide (4f), it may include N-hydroxymaleimide, N-hydroxysuccinimide, Endo-N-hydroxy-5-norbornene-2,3-dicarboxyimide, Endo-N-hydroxynorbornane-2,3-dicarboxyimide, Exo-N-hydroxy-7-oxabicyclo[2.2.1]hept-5-ene-2,3-dicarboxyimide and Exo-N-hydroxy-7-oxabicyclo[2.2.]heptane-2,3-dicarboxyimide.

Radiation-sensitive Resin Composition
(A) Radiation-sensitive Acid-generating Agent:

The acid-generating agent used as the component (A) in the second invention and third invention (hereinafter "acid-generating agent (A)" comprises the N-sulfonyloxyimide compound represented by the general formula (1). This N-sulfonyloxyimide compound may be used alone or in combination of two or more types.

(B) Resin Containing Acid-cleavable Group:

The resin used as component (B) in the second invention is an alkali-insoluble or alkali-slightly-soluble resin protected with an acid-cleavable group, the resin being capable of turning soluble in alkali upon cleavage of the acid-cleavable group (hereinafter "acid-cleavable group-containing resin (B)". This acid-cleavable group-containing resin (B) is a resin which is alkali-insoluble or alkali-slightly-soluble in itself, having been substituted with at least one acid-cleavable group capable of cleaving in the presence of an acid the hydrogen atom of an acidic functional group in a resin containing at least one acid-cleavable group such as a phenolic hydroxyl group or a carboxyl group as exemplified by an alkali-soluble resin having any of repeating units represented by the formulas (7-1) and (7-4) described later.

What is herein called "alkali-insoluble or alkali-slightly-soluble" is meant to be properties that, when, under alkaline development conditions employed in forming a resist pattern from a resist film formed using the radiation-sensitive resin composition containing the acid-cleavable group-containing resin (B), a film formed using only the acid-cleavable group-containing resin (B) is developed in place of the above resist film, the film thus developed remains by at least 50% of initial layer thickness after the development.

The acid-cleavable group in the acid-cleavable group-containing resin (B) may include, e.g., a substituted methyl group, a 1-substituted ethyl group, a 1-branched alkyl group, a silyl group, a germyl group, an alkoxycarbonyl group, an acyl group and a cyclic acid-cleavable group.

The substituted methyl group-may include, e.g., a methoxymethyl group, a methylthiomethyl group, an ethoxymethyl group, an ethylthiomethyl group, a methoxyethoxymethyl group, a benzyloxymethyl group, a benzylthomethyl group, a phenacyl group, a bromophenacyl group, a methoxyphenacyl group, a methylthioyphenacyl group, an α-methylphenacyl group, a cyclopropylmethyl group. a benzyl group, a diphenylmethyl group, a triphenylmethyl group, a bromobenzyl group, a nitrobenzyl group, a methoxybenzyl group, a methylthiobenzyl group, an ethoxybenzyl group, an ethylthiobenzyl group, a piperonyl group, a methoxycarbonylmethyl group, an ethoxycarbonylmethyl group, a n-propoxycarbonylmethyl group, an i-propoxycarbonylmethyl group, a n-butoxycarbonylmethyl group and a t-butoxycarbonylmethyl group.

The 1-substituted ethyl group may include, e.g., a 1-methoxyethyl group, a 1-methylthioethyl group, a 1,1-dimethoxyethyl group, a 1-ethoxyethyl group, a 1-ethylthioethyl group, a 1,1-diethoxyethyl group, a 1-ethoxypropyl group, a 1-propoxyethyl group, a 1-cyclohexyloxyethyl group, a 1-phenoxyethyl group, a 1-phenylthioethyl group, a 1,1-diphenoxyethyl group, a 1-benzyloxyethyl group. a 1-benzylthioethyl group, a 1-cyclopropylethyl group, a l-phenylethyl group, a 1,1-diphenylethyl group, a 1-methoxycarbonylethyl group, a 1-ethoxycarbonylethyl group, a 1-n-propoxycarbonylethyl group, a 1-isopropoxycarbonylethyl group, a 1-n-butoxycarbonylethyl group and a 1-t-butoxycarbonylethyl group.

The 1-branched alkyl group may include, e.g., an isopropyl group a sec-butyl group, a t-butyl group, a 1,1-dimethylpropyl group, a 1-methylbutyl group and a 1,1-dimethylbutyl group.

The silyl group may include, e.g., tricarbylsilyl groups such as trimethylsilyl group, an ethyldimethylsilyl group, a methyldiethylsilyl group, a triethylsilyl group, an i-propyldimethylsilyl group, a methyldi-i-propylsilyl group, a tri-i-propylsilyl group, a t-butyldimethylsilyl group, a methyldi-t-butylsilyl group, a tri-t-butylsilyl group, a phenyldimethylsilyl group, a methyldiphenylsilyl group and a triphenylsilyl group.

The germyl group may include, e.g., tricarbylgermyl groups such as a trimethylgermyl group, an ethyldimethylgermyl group, a methyldiethylgermyl group, a triethylgermyl group, an i-propyldimethylgermyl group, a methyldi-i-propylgermyl group, a tri-i-propylgermyl group, a t-butyldimethylgermyl group, a methyldi-t-butylgermyl group, a tri-t-butylgermyl group, a phenyldimethylgermyl group, a methyldiphenylgermyl group and a triphenylgermyl group.

The alkoxycarbonyl group may include, e.g., a methoxycarbonyl group, an ethoxycarbonyl group, an i-sopropoxycarbonyl group and a t-butoxycarbonyl group.

The acyl group may include, e.g., an acetyl group, a propionyl group, a butylyl group, a heptanoyl group, a hexanoyl group, a valeryl group, a pivaloyl group, an isovaleryl group, a lauroyl group, a myristoyl group, a palmitoyl group, a stearoyl group, an oxalyl group, a malonyl group, a succinyl group, a glutaryl group, an adipoyl group, a piperoyl group, a suberoyl group, a azelaoyl group, a sebacoyl group, an acryloyl group, a propioloyl group, a methacryloyl group, a chloronoyl group, an oleoyl group, a maleoyl group, a fumaroyl group, a methaconoyl group, a camphoroyl group, a benzoyl group, a phthaloyl group, an isophthaloyl group, a terephthaloyl group, a naphthoyl group, a toluoyl group, a hydroatropoyl group, an atropoyl group, a cinnamoyl group, a furoyl group, a thenoyl group, a nicotinoyl group, an isonicotinoyl group, a p-toluenesulfonyl group and a mesyl group.

The cyclic acid-cleavable group may include, e.g., a cyclopropyl group, a cyclopentyl group, a cyclohexyl group, a cyclohexenyl group, a 4-methoxycyclohexenyl group, a tetrahydropyranyl group, a tetrahydrofuranyl group, a tetrahydrothiopyranyl group, a tetrahydrothiofuranyl group, a 3-bromotetrahydropyranyl group, a 4-methoxytetrahydropyranyl group, a 4-methoxytetrahydrothiopyranyl group and a 3-tetrahydrothiophene-1,1-dioxide group.

Of these the acid-cleavable groups, a t-butyl group, a benzyl group, a 1-methoxyethyl group, a 1-ethoxylethyl group, a trimethylsilyl group, a t-butoxycarbonyl group, a t-butoxycarbonylmethyl group, a tetrahydropyranyl group, a tetrahydrofuranyl group, a tetrahydrothiopyranyl group and a tetrahydrothiofuranyl group are preferred.

The percentage of introduction of the acid-cleavable group in the acid-cleavable group-containing resin (B) [i.e., the proportion of the number of acid-cleavable groups to the total number of acidic functional groups and acid-cleavable groups which are not protected in the acid-cleavable group-containing resin (B)] depends on the types of the acid-cleavable group and an alkali-soluble resin into which the group is to be introduced, and can not absolutely be defined. It may preferably be from 10 to 100%, and more preferably from 15 to 100%.

The acid-cleavable group-containing resin (B) may preferably have a weight-average molecular weight (hereinafter "Mw") in terms of polystyrene as measured by gel permeation chromatography (GPC), of from 1,000 to 150,000, and more preferably from 3,000 to 100,000.

The acid-cleavable group-containing resin (B) may preferably have a ratio of the Mw to a number-average molecular weight (hereinafter "Mn") in terms of polystyrene as measured by gel permeation chromatography (GPC), Mw/Mn, of from 1 to 10, and more preferably from 1 to 5.

The acid-cleavable group-containing resin (B) may be produced by, e.g., introducing at least one acid-cleavable group in an alkali-soluble resin produced previously, or may be produced by poly- or copolymerization of at least one monomer having an acid-cleavable group, or poly- or copolycondensation of at least one polycondensation component having an acid-cleavable group.

The acid-cleavable group-containing resin (B) in the second invention may particularly preferably be a resin comprising a polymer or copolymer comprising poly (hydroxystyrene), a hydroxystyrene/hydroxy-α-methylstyrene copolymer, a hydroxystyrene/styrene copolymer or a copolymer of hydroxystyrene and/or hydroxy-α-methylstyrene with (meth)acrylate part or the whole of hydrogen atoms of phenolic hydroxyl groups or hydrogen atoms of carboxyl groups of which has been substituted with the acid-cleavable group(s).

The acid-cleavable group in the acid-cleavable group-containing resin (B) has also the property to control alkali solubility of the alkali-soluble resin, and has the action to lower or lose the effect of controlling the alkali solubility of the alkali-soluble resin or accelerate the alkali solubility of the alkali-soluble resin, upon cleavage of the acid-cleavable group in the presence of an acid.

In the second invention, the acid-cleavable group-containing resin (B) may be used alone or in the form of a mixture of two or more types.

(C) Alkali-soluble Resin:

The alkali-soluble resin used as component (C) in the third invention (hereinafter "alkali-soluble resin (C)" is et resin soluble in alkaline developing solutions having at least one functional group showing an affinity for alkaline developing solution, as exemplified by acidic functional groups such as a phenolic hydroxyl group and a carboxyl group.

The alkali-soluble resin (C) may include, e.g., addition polymerization resins having at least one of repeating units represented by the following formulas (7-1) to (7-3), and polycondensation resins having a repeating unit represented by the following formula (7-4).

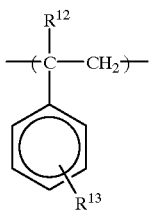

(7-1)

wherein in the formula (7-1), $R^{12}$ represents a hydrogen atom or a methyl group, $R^{13}$ represents —OH, —COOH, —$R^{14}$COOH, —O$R^{14}$OOH or —OCO$R^{14}$COOH (wherein $R^{14}$ represents —(CH$_2$)g—, where g represents an integer of 1 to 4.

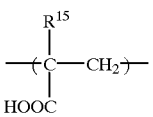

(7-2)

wherein in the formula (7-2), $R^{15}$ represents a hydrogen atom or a methyl group.

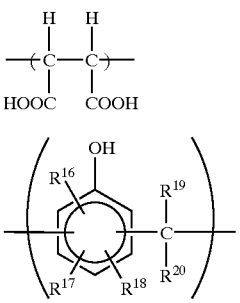

(7-3)

(7-4)

wherein in the formula (7-4), $R^{16}$, $R^{17}$, $R^{18}$, $R^{19}$ and $R^{20}$ each independently represent a hydrogen atom or an alkyl group having 1 to 4 carbon atoms.

In the case when the alkali-soluble resin (C) is an addition polymerization resin, it may be constituted of only any of the repeating units represented by the formulas (7-1) to (7-3). It may further have additional repeating unit(s) as long as the resin formed is soluble in alkaline developing solutions.

Such additional repeating unit(s) may include, e.g., units formed by participation in addition polymerization, of a polymerizable double-bond moiety of a monomer having double bonds as exemplified by styrene, α-methylstyrene, maleic anhydride, (meth)acrylonitrile, crotonnitrile, maleinnitrile, fumaronitrile, mesaconnitrile, citraconnitrile, itaconnitrile, (meth)acrylamide, crotonamide, maleinamide, fumaramide, mesaconamide, cytroconamide, itaconamide, vinylaniline, vinylpyrdine, vinyl-_-caprolactum, vinylpyrrolidone and vinylimidazole.

The addition polymerization resin may be produced by subjecting at least one monomers corresponding to the repeating units represented by the formulas (7-1) to (7-3), to polymerization or copolymerization optionally together with a monomer or monomers corresponding to the additional repeating unit(s).

Such polymerization or copolymerization may be carried out by any of appropriate, conventionally known polymerization, processes such as bulk polymerization, solution polymerization, precipitation polymerization, emulsion polymerization, suspension polymerization and bulk-suspension polymerization under appropriate selection of a polymerization initiator or polymerization catalyst such as a radical polymerization initiator, an anionic polymerization catalyst, a coordination anionic polymerization catalyst or a cationic polymerization catalyst in accordance with the types of monomers, reaction mediums and so forth.

In the case when the alkali-soluble resin (C) is a polycondensation resin, it may be constituted of only the repeating unit represented by the formula (7-4). It may further have additional repeating unit(s) as long as the resin formed is soluble in alkaline developing solutions.

Such polycondensation resin may be produced by subjecting at least one phenol and at least one aldehyde corresponding to the repeating unit represented by the formula (7-4), to polycondensation or copolycondensation optionally together with a polycondensation component capable of forming the additional repeating unit(s), in the presence of an acidic catalyst in an aqueous medium or a mixed medium of water and a hydrophilic solvent.

The phenol may include, e.g., o-cresol, m-cresol, p-cresol, 2.3-xylenol, 2,4-xylenol, 2,5-xylenol, 3,4-xylenol, 3,5-xylenol, 2,3,5-trimethylphenol and 3,4,5-trimethylphenol. The aldehyde may include, e.g., formaldehyde, trioxane, paraformaldehyde, benzaldehyde, acetaldehyde, propylaldehyde and phenylacetaldehyde.

The content of the repeating units represented by the formulas (7-1) to (7-4) in the alkali-soluble resin (C) depends on the types of the additional repeating unit(s) optionally contained and can not absolutely be defined. It may preferably be from 10 to 100 mole %, and more preferably from 20 to 100 mole %.

The alkali-soluble resin (C) may preferably have an Mwr of from 1,000 to 150,000, and more preferably from 3,000 to 100,000, which may vary in accordance with the desired properties of the radiation-sensitive resin composition.

The alkali-soluble resin (C) may usually have an Mw/Mn of from 1 to 10, and preferably from 1 to 5.

The alkali-soluble resin (C), when it has the repeating units containing carbon-carbon unsaturated bonds as represented by the formulas (7-1) to (7-4), may also be used as a hydrogenated product. In such a case, the degree of hydrogenation may usually be not more than 70%, preferably not more than 50%. and more preferably not more than 40%, of the carbon-carbon unsaturated bonds contained in the repeating units represented by the formulas (7-1) to (7-4). Here, if the degree of hydrogenation is more than 70%, there is a possibility that the developability of the alkali-soluble resin (C) with the alkaline developing solution is lowered.

The alkali-soluble resin (C) may particularly preferably be a resin composed chiefly of poly(hydroxystyrene), a hydroxystyrene/hydroxy-α-methylstyrene copolymer or a hydroxystyrene/styrene copolymer.

The alkali-soluble resin (C) may be used alone or in the form of a mixture of two or more types.

Cross-linking Agent:

What is used as component (D) in the third invention is a compound capable of cross-linking the alkali-soluble resin (C) in the presence of an acid, e.g., an acid generated by exposure (hereinafter "cross-linking agent (D)"). The cross-linking agent (D) may include, e.g., compounds having at least one substituent having cross-linking reactivity with the alkali-soluble resin (C) (hereinafter "cross-linkable substituent".

The cross-linkable substituent in the cross-linking agent (D) may include groups represented by the following formulas (8-1) to (8-5).

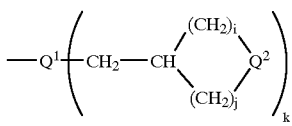  (8-1)

wherein in the formula (8-1), k is 1 or 2, $Q^1$ represents a single bond, —O—, —S—, —COO— or —NH— when k is 1, or represents a trivalent nitrogen atom when k is 2; $Q^2$ represents —O— or —S—; and i represents an integer of 0 to 3, and j an integer of 1 to 3, where i+j=1 to 4.

$$—[—C(R^{21})(R^{22})—]_y—Q^3—R^{23} \quad (8\text{-}2)$$

wherein in the formula (8-2), $Q^3$ represents —O—, —S—, —COO— or —CO—; $R^{21}$ and $R^{22}$ each independently represent a hydrogen atom or an alkyl group having 1 to 4 carbon atoms; $R^{23}$ represents an alkyl group having 1 to 4 carbon atoms, an aryl group having 6 to 12 carbon atoms or an aralkyl group having 7 to 14 carbon atoms; an y is an integer of 1 or more.

$$—C(R^{24})=C(R^{25})(R^{26}) \quad (8\text{-}3)$$

wherein in the formula (8-3), $R^{24}$, $R^{25}$ and $R^{26}$ each independently represent a hydrogen atom or an alkyl group having 1 to 4 carbon atoms.

$$—[—C(R^{21})(R^{22})—]_y—N(R^{27})(R^{28}) \quad (8\text{-}4)$$

wherein in the formula (8-4), $R^{21}$ and $R^{22}$ have the same definition as the $R^{21}$ and $R^{22}$ in the formula (8-2), $R^{27}$ and $R^{28}$ each independently represent a hydrogen atom or an alkyloyl group having 1 to 5 carbon atoms, and y is an integer of 1 or more.

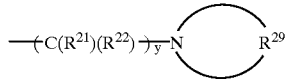  (8-5)

wherein in the formula (8-5), $R^{21}$ and $R^{22}$ have the same definition as the $R^{21}$ and $R^{22}$ in the formula (8-2); $R^{29}$ represents a divalent organic group having a hetero atom of any of an oxygen atom, a sulfur atom and a nitrogen atom and forming a 3 to 8-membered ring; and y is an integer of 1 or more.

As specific examples of such a cross-linkable substituent, it may include a glycidyloxy group, a glycidyloxycarbonyl group, a glycidylamino group, a methoxymethyl group, an ethoxymethyl group, a benzyloxymethyl group, a dimethylaminomethyl group, a diethylaminomethyl group, a dimethylolaminomethyl group, a diethylolaminomethyl group, a morpholinomethyl group, an acetoxymethyl group, a benzolyloxymethyl group, a formyl group, an acetyl group, a vinyl group and an isopropenyl group.

The cross-linking agent (D) may include, e.g., bisphenol-A epoxy compounds, bisphenol-F epoxy compounds, bisphenol-S epoxy compounds, novolak resin epoxy compounds, resol resin epoxy compounds, poly(hydroxystyrene) epoxy compounds, methylol group-containing melamine compounds, methylol group-containing benzoguanamine compounds, methylol group-containing urea compounds, methylol group-containing phenolic compounds, alkoxyalkyl group-containing melamine compounds, alkoxyalkyl group-containing benzoguanamine compounds, alkoxyalkyl group-containing urea compounds, alkoxyalkyl group-containing phenolic compounds, carboxymethyl group-containing melamine resins, carboxymethyl group-containing benzoguanamine resins, carboxymethyl group-containing urea resins, carboxymethyl group-containing phenolic resins, carboxymethyl group-containing melamine compounds, carboxymethyl group-containing benzoguanamine compounds, carboxymethyl group-containing urea compounds and carboxymethyl group-containing phenolic compounds.

Of these cross-linking agent (D) compounds, preferred are methylol group-containing phenolic compounds, methoxymethyl group-containing melamine compounds, methoxymethyl group-containing phenolic compounds, methoxymethyl group-containing glycoluril compounds, methoxymethyl group-containing urea compounds and acetoxymethyl group-containing phenolic compounds. More preferred are methoxymethyl group-containing melamine compounds (e.g., hexamethoxymethylmelamine), methoxymethyl group-containing glycoluril compounds and methoxymethyl group-containing urea compounds. The methoxymethyl group-containing melamine compounds are commercially available under trade names such as CYMEL300, CYMEL301, CYMEL303 and CYMEL305 (products of Mitsui Cyanamide Co.). The methoxymethyl group-containing glycoluril compounds are commercially available under trade names such as CYMEL1174 (a product of Mitsui Cyanamide Co.). Also, the methoxymethyl group-containing urea compounds are commercially available under trade names such as MX290 (a product of Sanwa Chemical Co., Ltd.).

As the cross-linking agent (D), also preferably usable are compounds obtained by introducing the cross-linkable substituent into an acidic functional group in the alkali-soluble resin (C) so as to be endowed with the properties as the cross-linking agent (D). In such a case, the percentage of introduction of the cross-linkable substituent (functional group) depends on the types of the cross-linkable substituent (functional group) and the alkali- soluble resin (C) into which the group is to be introduced, and can not absolutely be defined. It may usually be from 5 to 60 mole %, preferably from 10 to 50 mole %, and more preferably from 15 to 40 mole %. Here, if the percentage of introduction of the cross-linkable substituent (functional group) is less than 5 mole %, there tends to be caused, e.g., a lowering of the yield of residual film thickness and a slimming or swelling of patterns. If it is more than 60 mole %, developability tends to be lowered.

The cross-linking agent (D) in the third invention may particularly preferably be a methoxymethyl group-containing glycoluril compound or a methoxymethyl group-containing urea compound, stated specifically, tetramethoxymethyl glycoluril or dimethoxymethyl urea.

In the third invention, the cross-linking agent (D) may be used alone or in the form of a mixture of two or more types.

Mixing proportion of the respective components that constitute the positive radiation-sensitive resin composition of the second invention and mixing proportion of the respective components that constitute the negative radiation-sensitive resin composition of the third invention may vary in accordance with the desired characteristics of resists. To show examples of the mixing proportions, they are as follows:

In the second invention, the acid-generating agent (A) may usually be mixed in an amount of from 0.001 to 70 parts by weight, preferably from 0.01 to 50 parts by weight, and particularly preferably from 0.1 to 20 parts by weight, based on 100 parts by weight of the acid-cleavable group-containing resin (B). Here, if the acid-generating agent (A) is mixed in an amount less than 0.001 part by weight, the resultant composition may have low sensitivity and resolution. If on the other hand it is more than 70 parts by weight, resist coating performance and pattern shape tend to deteriorate.

Then, in the third invention, the acid-generating agent (A) may usually be mixed in an amount of from 0.001 to 70 parts by weight, preferably from 0.01 to 50 parts by weight, and particularly preferably from 0.1 to 20 parts by weight, based on 100 parts by weight of the alkali-soluble resin (C). Here, if the acid-generating agent (A) is mixed in an amount less than 0.001 part by weight, the resultant composition may have low sensitivity and resolution. If on the other hand it is more than 70 parts by weight, resist coating performance and pattern shape tend to deteriorate.

As for the cross-linking agent (D), it may usually be mixed in an amount of from 5 to 95 parts by weight, preferably from 15 to 85 parts by weight, and particularly preferably from 20 to 75 parts by weight, based on 100 parts by weight of the alkali-soluble resin (C). Here, if the cross-linking agent (D) is mixed in an amount less than 5 parts by weight, there tends to be caused, e.g., a lowering of the yield of residual film thickness and a meandering or swelling of patterns. If on the other hand it is more than 95 parts by weight, the resultant composition may have a low developability.

Additives:

In the positive radiation-sensitive resin composition of the second invention and the negative radiation-sensitive resin composition of the third invention, various additives such as a radiation-sensitive acid-generating agent other than, the acid-generating agent (A) (hereinafter "additional acid-generating agent"), an acid diffusion control agent, a surface-active agent and a sensitizer may optionally be mixed. In the positive radiation-sensitive resin composition of the second invention, the alkali-soluble resin (C) and/or a low-molecular weight alkali-solubility control agent having anacid-cleavableprotectivegroupmayfurtherbemixed- Also, in negative radiation-sensitive resin composition of the third invention, the acid-cleavable group-containing resin (B) may further be mixed.

The additional acid-generating agent may preferably be an onium salt compound. Particularly preferred are diphenyliodonium trifluoromethane sulfonate, diphenyliodonium nonafluoro-n-butane sulfonate, diphenyliodonium 10-camphor sulfonate, bis(4-t-butylphenyl)jodonium trifluoromethane sulfonate, bis(4-t-butylphenyl)iodonium nonafluoro-n-butane sulfonate, bis(4-t-butylphenyl) iodonium camphor sulfonate, triphenylsulfonium trifluoromethane sulfonate, triphenylsulfonium nonafluoro-n-butane sulfonate, oor triphenylsulfonium 10-camphor sulfonate.

In addition to the onium salt compound, also usable are halogen-containing compounds, sulfonate compounds, quinonediazide compounds, sulfonimide compounds and diazomethane compounds.

Any of these additional acid-generating agents may be used alone or in the form of a mixture of two or more types.

Mixing proportion of the additional acid-generating agent is appropriately selected in accordance with the types of acid-generating agents, and may preferably be in an mount of from 95 parts by weight or less, and more preferably 90 parts by weight or less, based on 100 parts by weight of the total weight of the the acid-generating agent (A) and additional acid-generating agent. Here, if the additional acid-generating agent is in a mixing proportion more than 95 parts by weight, the effect intended in the present invention tends to lower.

In the second invention and third invention, an acid diffusion control agent may further be mixed which has the action to control a phenomenon where the acid generated from the acid-generating agent (A) or additional acid-generatirng agent upon exposure diffuses into resist films and to control any unwanted chemical reaction in unexposed areas.

Use of such an acid diffusion control agent brings about an improvement in storage stability of the resin composition and an improvement in resolution as a resist, and also can keep resist pattern line width from changing because of variations of a post exposure delay (PED), of from exposure to developing treatment, promising a very good processing stability.

The acid diffusion control agent may preferably be a nitrogen-containing organic compound that may cause no change in basicity as a result of exposure or heat treatment in the course of the formation of resist patterns.

Such a nitrogen-containing organic compound may include, e.g., compounds represented by the following formula (9):

wherein in the formula (9), $R^{30}$, $R^{31}$ and $R^{32}$ each independently represent a hydrogen atom, a substituted or unsubstituted alkyl group, a substituted or unsubstituted aryl group or a substituted or unsubstituted aralkyl group (hereinafter "nitrogen-containing compound (I)"), diamino compounds having two nitrogen atoms in the same molecule (hereinafter "nitrogen-containing compound (II)"), diamino polymers having three or more nitrogen atoms (hereinafter "nitrogen-containing compound (III)"), amide group-containing compounds, urea compounds, and nitrogen-containing heterocyclic compounds.

The nitrogen-containing compound (I) may include, e.g., monoalkylamines such as n-hexylamine, n-heptylamine, n-octylamine, n-nonylamine and n-decylamine; dialkylamines such as di-n-butylamine, di-n-pentylamine, di-n-hexylamine, di-n-heptylamine, di-n-octylamine, di-n-nonylamine and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine and tri-n-decylamine; aromatic amines such as aniline, N-methylaniline, N,N-dimethylaniline, 2-methylaniline, 3-methylaniline, 4-methylaniline, 4-nitroaniline, diphenylamine, triphenylamine and 1-naphthylamine; and alkanolamines such as ethanolamine, diethanolamine and triethanolamine.

The nitrogen-containing compound (II) may include, e.g., ethylenediamine, N,N,N',N'-tetramethylethylenediamine, tetramethylenediamine, hexamethylenediamine, N,N,N',N'-tetrakis(2-hydroxyethyl)ethylenediarine, N,N,N',N'-tetrakis(2-hydroxypropyl)ethylenediamine, 4,4'-diaminophenylmethane, 4,4'-diaminodiphenylether, 4,4'-diaminobenzophenone, 4,4'-diaminodiphenylamine, 2,2'-bis (4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4- hydroxyphenyl)propane, 1,4-bis[1-(4-aminophenyl)-1-methylethyl]benzene, and 1,3-bis[1-(4-aminophenyl)-1-methylethyl]benzene.

The nitrogen-containing compound (III) may include, e.g., polymers such as polyethyleneimine, polyallylamine and dimethylaminoethyl acrylamide.

The amide group-containing compounds may include, e.g., formamide, N-methylformamide, N,N-dimethylformamide, acetamide, N-methylacetamide, N,N-dimethylacetamide, propionamide, benzamide, pyrrolidone and N-methylpyrrolidone.

The urea compounds may include, e.g., urea, methylurea, 1,1-dimethylurea, 1,3-dimethylurea, 1,1,3,3-tetramethylurea, 1,3-diphenylurea and tributylthiourea.

The nitrogen-containing heterocyclic compounds may include, e.g., imidazoles such as imidazole, benzimidazole, 2-methylimidazole, 4-methylimidazole, 2-phenylimidazole, 4-phenylimidazole and 4-methyl-2-phenylimidazole; pyridines such as pyridine, 2-methylpyridine, 4-methylpyridine, 2-ethylpyridine, 4-ethylpyridine, 2-phenylpyridine, 4-phenylpyridine, N-methyl-4-phenylpyridine, nicotine, nicotinic acid, nicotinic acid amide, quinoline, 8-oxaquinoline and acrydine; and besides pyrazine, pyrazole, pyridazine, quinozaline, purine, pyrrolidine, piperidine, morpholine, 4-methylmorpholine, piperadine, 1,4-dimethylpiperadine and 1,4-diazabicyclo[2.2.2]octane.

Of these nitrogen-containing organic compounds, the nitrogen-containing compound (I) and the nitrogen-containing heterocyclic compounds are preferred. Also, of the nitrogen-containing compound (I), pyridines are particularly preferred.

The acid diffusion control agent may be used alone or in the form of a mixture of two or more types.

The acid diffusion control agent may preferably be mixed in an amount not more than 15 parts by weight, more preferably from 0.001 to 10 parts by weight, and particularly preferably from 0.005 to 5 parts by weight, based on 100 parts by weight of the acid-cleavable group-containing resin (B) or alkali-soluble resin (C). Here, if the acid diffusion control agent is mixed in an amount more than 15 parts by weight, the sensitivity and developability required as resists tend to lower. Incidentally, if the acid diffusion control agent is mixed in an amount smaller than 0.001 part by weight, there is a possibility of a lowering of pattern shape quality and dimensional faithfulness required as resists.

The surface-active agent has the action to improve the coating performance, striation, developability and so forth. Such a surface-active agent includes anionic, cationic, non-ionic and amphoteric types, any of which may be used. Preferred surface-active agents are nonionic surface-active agents.

As examples of the nonionic surface-active agents they may include polyoxyethylene higher alkyl ethers, polyoxyethylene higher alkyl phenyl ethers, polyethylene glycol higher fatty acid diethers, and besides a series of products with trade names such as KP (available from Shin-Etsu Chemical Co., Ltd.), POLYFLOW (available from Kyoueisha Chemical Co., Ltd.), F-TOP (available from Tohchem Products Co.) MEGAFACK (available from Dainippon Ink & Chemicals, Inc.), FLUORAD (available from Sumitomo 3M Limited), and ASAHI GUARD and SURFLON (available from Asahi Glass Co., Ltd.

Any of these surface-active agents may be used alone or in the form of a mixture of two or more types.

The surface-active agent may usually be mixed in an amount not more than 2 parts by weight as an effective component of the surface-active agent, based on 100 parts by weight of the total resin components in the radiation-sensitive resin composition.

The sensitizer shows the action to absorb the energy of radiations and transmit the absorbed energy to the acid-generating agent (A) or the additional acid-generating agent to cause the acid to be generated in a large quantity, and has the effect of improving apparent sensitivity of the radiation-sensitive resin composition.

Preferred sensitizers are acetophenones, benzophenones, naphthalenes, biacetyl, eosine, Rose Bengale, pyrenes, anthracenes and phenothiazines.

Any of these sensitizers may be used alone or in the form of a mixture of two or more types. The sensitizer may usually be mixed in an amount not more than 50 parts by weight, and preferably not more than 30 parts by weight, based on 100 parts by weight of the total resin components in the radiation-sensitive resin composition.

A dye or pigment may also be mixed so that latent images at exposed areas can be rendered visible and any influence of halation can be lessened at the time of exposure, and an adhesion aid may be mixed so as to improve adhesion to substrates.

As other additives, they may further be halation preventive agents, storage stabilizers, anti-foaming agents and shape improvers, which may specifically include 4-hydroxy-4'-methylcalcon.

Solvents:

The second-invention positive radiation-sensitive resin composition and the third-invention negative radiation-sensitive resin composition are, when used, each dissolved in a solvent so as to be in a solid concentration of, e.g., from 5 to 50% by weight, followed by filtration with a filter having a pore size of, e.g., about 0.2 µm, and prepared into composition solutions.

The solvent may include, e.g., ethers, esters, ether esters, ketones, ketone esters, amides, amide esters, lactams, lactones, and (halogenated) hydrocarbons, and may more specifically include ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, acetates, hydroxyacetates, lactates, alkoxyacetates, cyclic or non-cyclic ketones, acetoacetates, piruvates, propionates, N,N-dialkylformamides, N,N-dialkylacetamides, N-alkylpyrrolidones, y-lactones, (halogenated) aliphatic hydrocarbons, and (halogenated) aromatic hydrocarbons.

As specific examples of such solvents, they may include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, propylene glycol monomethyl ether acetate, propylene glycol monoethyl ether acetate, propylene glycol mono-n-propyl ether acetate, isopropenyl acetate, isopropenyl propionate, toluene, xylene, methyl ethyl ketone, cyclohexanone, 2-heptane, 3-heptane, 4-heptane, ethyl 2-hydroxypropionate, ethyl 2-hydroxy-2-methylpropionate, ethyl ethoxyacetate, ethyl hydroxyacetate, methyl 2-hydroxy-3-methylbutyrate, methyl lactate, ethyl lactate, n-propyl lactate, i-propyl lactate, 3-methoxybutyl acetate, 3-methyl-3-methoxybutyl acetate, 3-methyl-3-methoxybutyl propionate, 3-methyl-3-methoxybutyl butyrate, ethyl acetate, n-propyl acetate, n-butyl acetate, methyl acetoacetate, ethyl acetoacetate, methyl 3-methoxypropionate, ethyl 3-methoxypropionate, methyl 3-ethoxypropionate, ethyl 3-ethoxypropionate, N-methylpyrrolidone, N,N-dimethylformamide and N,N-dimethylacetamide.

Of these solvents, propylene glycol monoalkyl ether acetates, 2-heptane, lactates, 2-hydroxypropionates and 3-alkoxypropionates are preferred.

The above solvents may be used alone or in the form of a mixture of two or more types.

To the above solvent, at least one high-boiling point solvent may optionally be added, such as benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butylolactone, ethylene carbide, propylene carbide, and ethylene glycol monophenyl ether acetate.

Formation of Resist Pattern:

When resist patterns are formed using the second-invention positive radiation-sensitive resin composition and the third-invention negative radiation-sensitive resin composition, the composition solutions prepared as described previously may be coated on, e.g., substrates such as silicon wafers or wafers covered with aluminum, by coating means such as spin coating, cast coating or roll coating to form resist films, followed by heat treatment (hereinafter this heat treatment is called "PB"), and then the resist films are subjected to exposure through given mask patterns. Radiations usable for the exposure may include mercury lamp bright-line spectra (wavelength: 254 nm), far-ultraviolet radiations of KrF excimer lasers (wavelength: 248 nm) or ArF excimer lasers (wavelength: 193 nm), X-radiations such as synchrotron radiations, and charged-particle radiations such as electron radiations. Far-ultraviolet radiations and charged-particle radiations are preferred. In particular, radiations of KrF excimer lasers (wavelength: 248 nm) or ArF excimer lasers (wavelength: 193 nm) and electrons are preferred. Exposure conditions such as; radiation dose may appropriately be selected in accordance with the mixing formulation and additives for the radiation-sensitive resin compositions.

After exposure, heat treatment to improve apparent sensitivity of resists (this heat treatment is hereinafter called "PEB") may preferably be made. Heating conditions in such a case may vary depending on the mixing formulation and additives for the radiation-sensitive resin compositions. Usually, the heating may be be at a temperature of from 30 to 200° C., and preferably from 50 to 150° C.

Thereafter, the resist is developed with an alkaline developing solution to form a stated resist pattern.

As the alkaline developing solution, usable are, e.g., alkaline aqueous solutions prepared by dissolving at least one of alkaline compounds such as alkali metal hydroxides, ammonia water, alkylamines, alkanolamines, heterocyclic amines, tetraalkylammonium hydroxides, choline, 1,8-diazabicyclo[5.4.0]-7-undecene and 1,5-diazabicyclo[4.3.0]-5-nonene so as to be in a concentration of usually from 1 to 10% by weight, and preferably from 2 to 5% by weight. Particularly preferred alkaline developing solutions are aqueous solutions of tetraalkylammonium hydroxides.

To developing solutions formed of such alkaline aqueous solutions, water-soluble organic solvents or surface-active agents as exemplified by methanol and ethanol may also be added in appropriate quantity.

Incidentally, when such developing solutions formed of alkaline aqueous solutions are used, it is common to carry out: water washing after the development.

EXAMPLES

The present invention will be described below in greater detail by giving Examples. The present invention should by no means be construed limitative by these Examples.

Synthesis of N-sulfonyloxyimide Compound

Synthesis Example 1

Usual Diels-Alder reaction of methyl acrylate with cyclopentadiene in equimolar quantities was effected to synthesize a compound represented by the following formula (10-1) (hereinafter "compound (α1)").

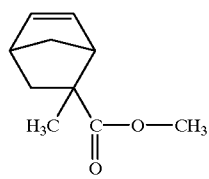

(10-1)

In a flask holding therein 100 g (0.6 mole) of the compound (α1), 8.5 g of 2,2-azobisisobutyronitrile (AIBN) and 208 g of sodium bisulfite (a commercially available product), 1,000 ml of methanol and 300 ml of distilled water were added, and these were refluxed for 2 hours with stirring. Thereafter, the reaction solution obtained was cooled to room temperature, and. 1,500 ml of distilled water was added and then the methanol was removed under reduced pressure. Thereafter, the remaining aqueous solution was filtered, followed by extraction with 1,000 ml of ethyl ether. Then, to the transparent aqueous solution obtained, 420 g of sodium chloride was added and then stirred overnight at room temperature. Thereafter, the aqueous solution was filtered, and the precipitate obtained was washed with a small amount of a saturated aqueous sodium chloride solution three times. Then the precipitate thus washed was dried at 55° C. for 12 hours under normal pressure to obtain 225 g of a crude product. This crude product was extracted with 1,800 ml of methanol to obtain a solid matter, which was further extracted with 500 ml of methanol to obtain 74 g of a compound represented by the following formula (10-2) (hereinafter "compound (α2)").

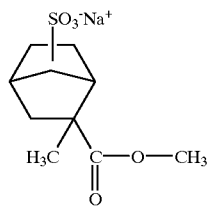

(10-2)

Next, in a flask holding therein 10 g of the compound (α2) and 12 ml of dimethylformamide, 4 ml of thionyl chloride was slowly dropwise added with stirring, followed by stirring at room temperature for 1.5 hours. Thereafter, 200 ml of ice water was quickly poured into the reaction solution, and the oil having come to precipitate was stirred to cause to solidify. Subsequently, the upper layer aqueous solution was discarded, and the solidified matter was dissolved in 100 ml of methylene chloride. The resultant solution was washed with 100 ml of an aqueous 10% sodium carbonate solution and 100 ml of an aqueous, 10% sodium chloride solution, and then dried with sodium sulfate. Thereafter, the methylene chloride was removed under reduced pressure, followed by vacuum drying at room temperature to obtain 9.2 g of sulfonic acid chloride represented by the following formula (10-3) (hereinafter "compound (α3)").

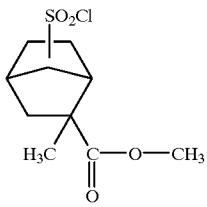
(10-3)

Next, in a flask holding therein 9.2 g of the compound (α3) and 7.4 g of endo-N-hydroxy-5-norbornene-2,3-dicaroboxyimide, 50 ml of dimethylformamide was added with stirring, and then 10 ml of triethylamine was dropwise added, followed by stirring at room temperature for 8 hours. Thereafter, 500 ml of water was poured into the reaction solution, so that oil became precipitated. After cooling on an ice bath, the upper layer aqueous solution was discarded, and the remaining oil was dissolved in 100 ml of methylene chloride. The resultant solution was washed with 100 ml of an aqueous 10% sodium sodium chloride solution, and then dried with sodium sulfate. Thereafter, the methylene chloride was concentrated under reduced pressure, followed by column chromatography (solvent: 3% methanol/methylene chloride) using silica gel, to obtain 4.2 g of an N-sulfoxyimide compound represented by the following formula (10-4) (molecular formula: $C_{19}H_{23}NO_7S$; hereinafter "PAG1").

Elementary analysis of carbon and hydrogen of the PAG1 revealed values (% by weight) of 55.59 of carbon (theoretical value: 55.73), 5.75 of hydrogen (theoretical value: 5.66) and 3.51 of nitrogen (theoretical value: 3.42).

Figure 2:
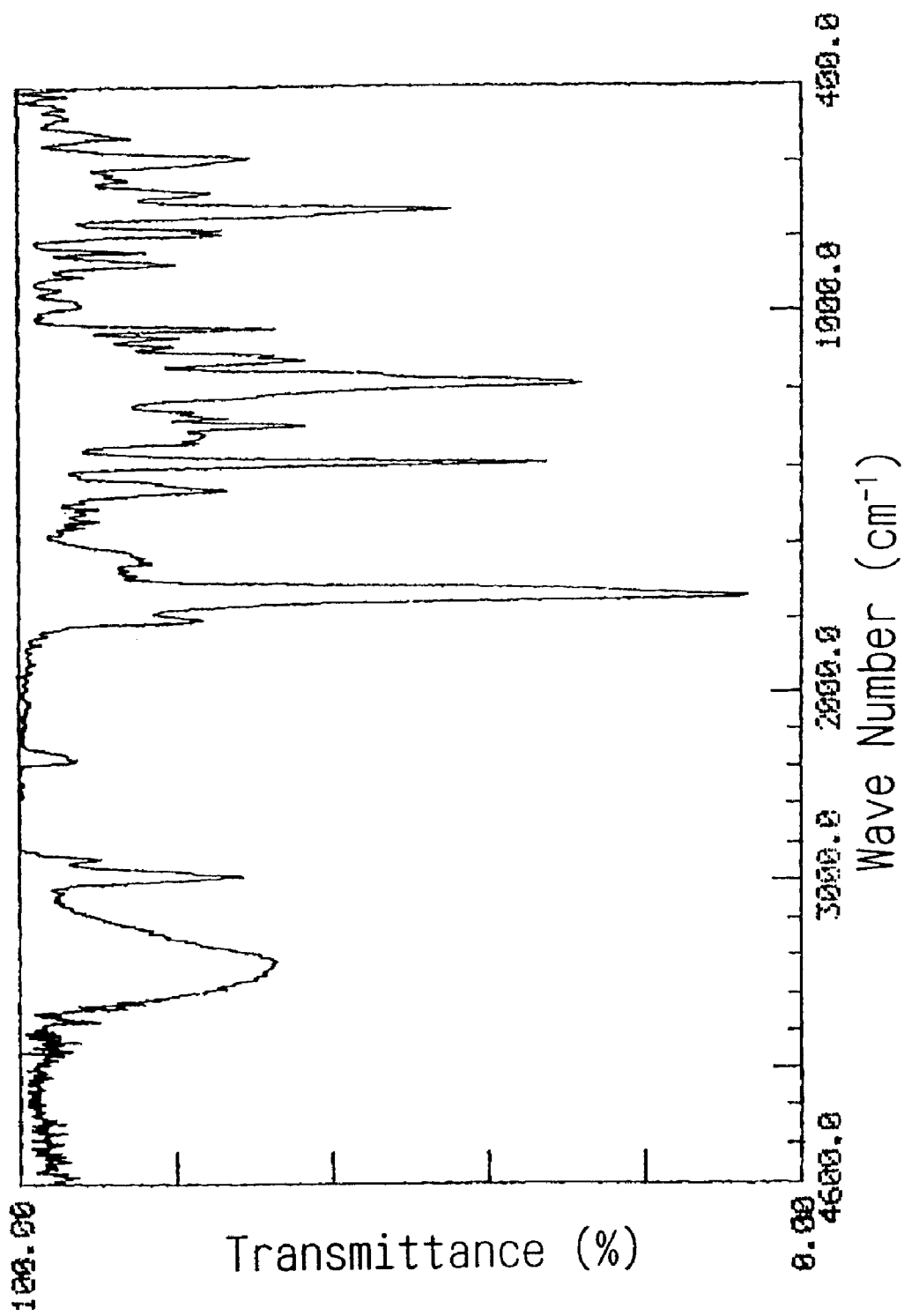
FIG. 2 is a graph showing the results of measurement of infrared spectra of the N-sulfonyloxyimide compound (PAG1) obtained in Synthesis Example 1.
Figure 3:
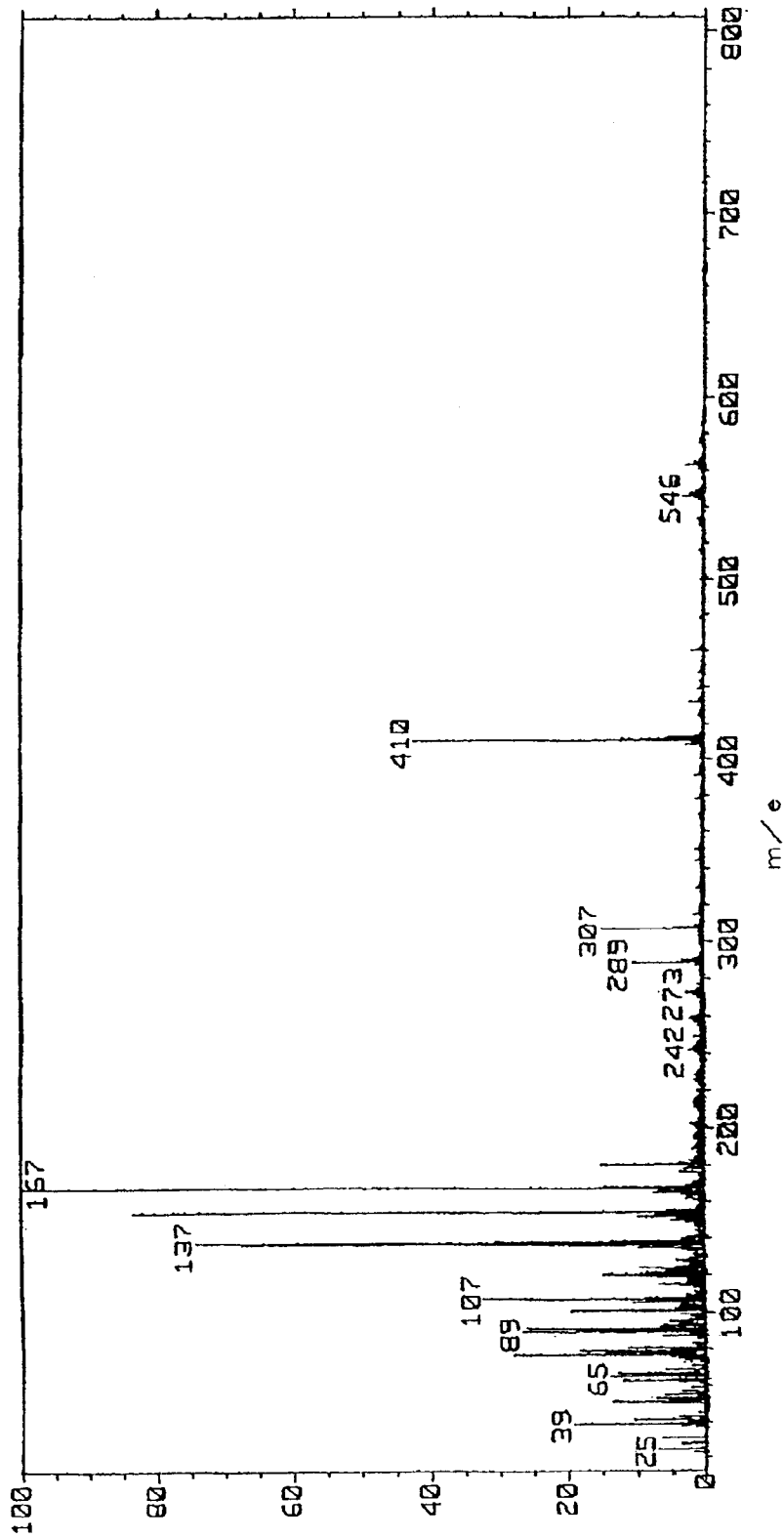
FIG. 3 is a graph showing the results of measurement by fast atom bombardment mass spectrometry of the N-sulfonyloxyimide compound (PAG1) obtained in Synthesis Example 1.

The PAG1 was also put to $^1$H-NMR analysis (solvent: acetone-$d_6$; the same applies hereinafter), infrared absorption spectrometry, and fast atom bombardment mass spectrometry (matrix: 3-nitrobenzyl alcohol; the same applies hereinafter) (M+H$^+$=410) to obtain measurement results shown in FIGS. 1, 2 and 3, respectively.

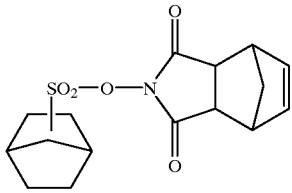
(10-4)

Synthesis Example 2

Reaction and post-treatment were carried out in the same manner as in Synthesis Example 1 except for using 5 g of N-hydroxysuccinimide, to obtain 3.9 g of a sulfoxyimide compound represented by the following formula (11) (molecular formula: $C_{14}H_{19}NO_7S$; hereinafter "PAG2").

Elementary analysis of carbon and hydrogen of the PAG2 revealed values (% by weight) of 48.77 of carbon (theoretical value: 48.69), 5.59 of hydrogen (theoretical value: 5.55) and 4.02 of nitrogen (theoretical value: 4.06).

Figure 4:
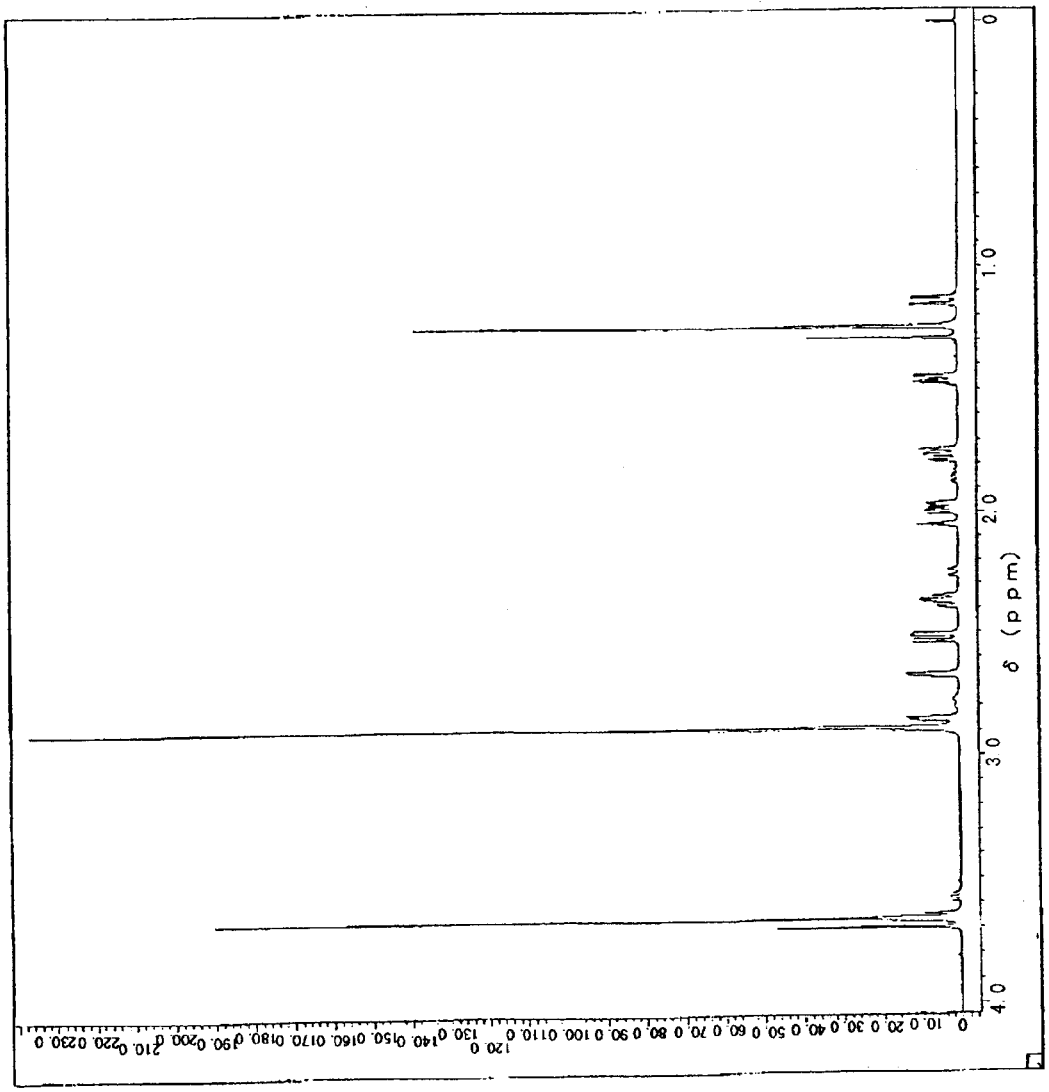
FIG. 4 is a graph showing the results of measurement by $^1$H-NMR analysis of an N-sulfonyloxyimide compound (PAG2) obtained in Synthesis Example 2.
Figure 5:
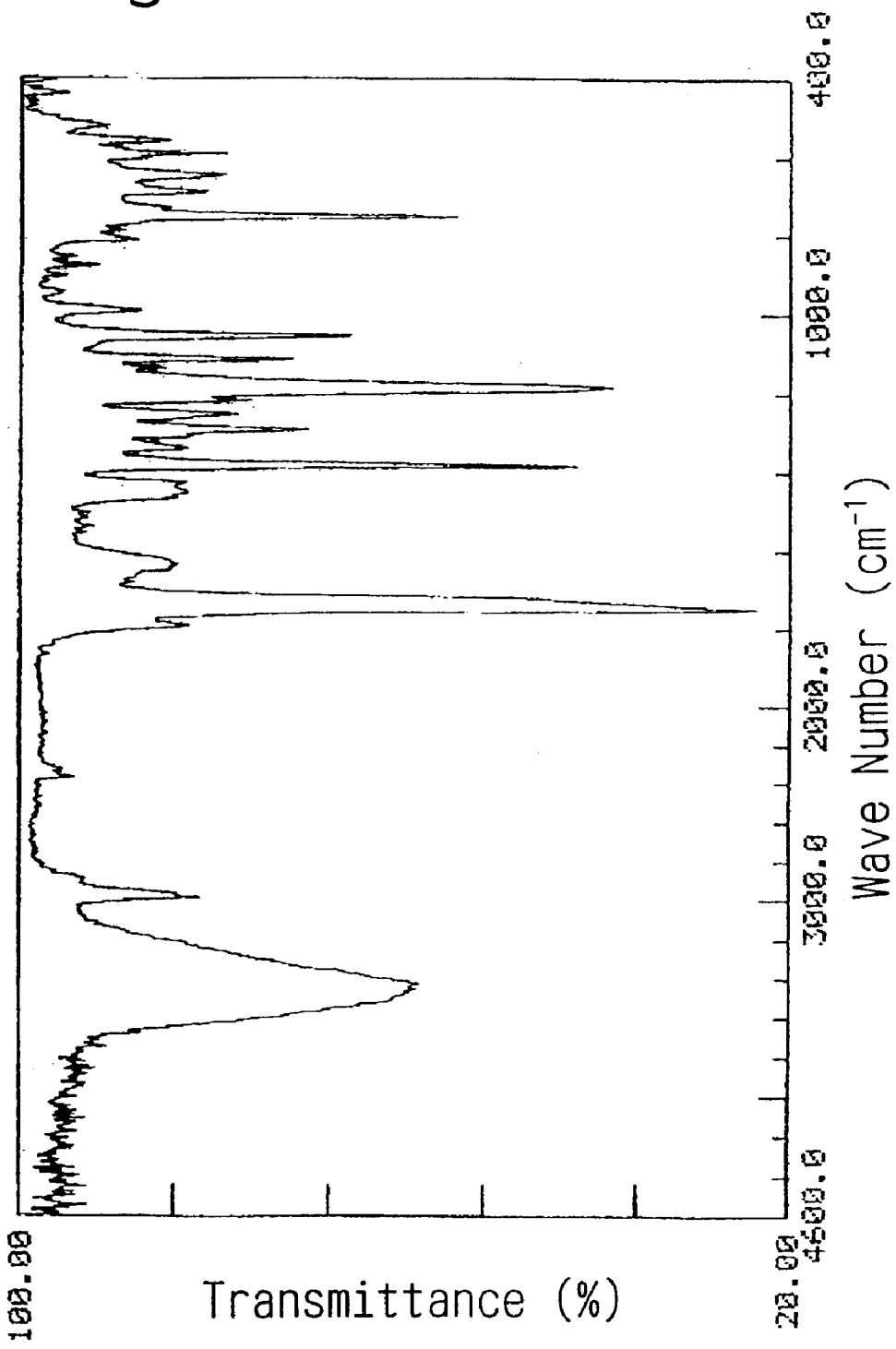
FIG. 5 is a graph showing the results of measurement of infrared spectra of the N-sulfonyloxyimide compound (PAG2) obtained in Synthesis Example 2.
Figure 6:
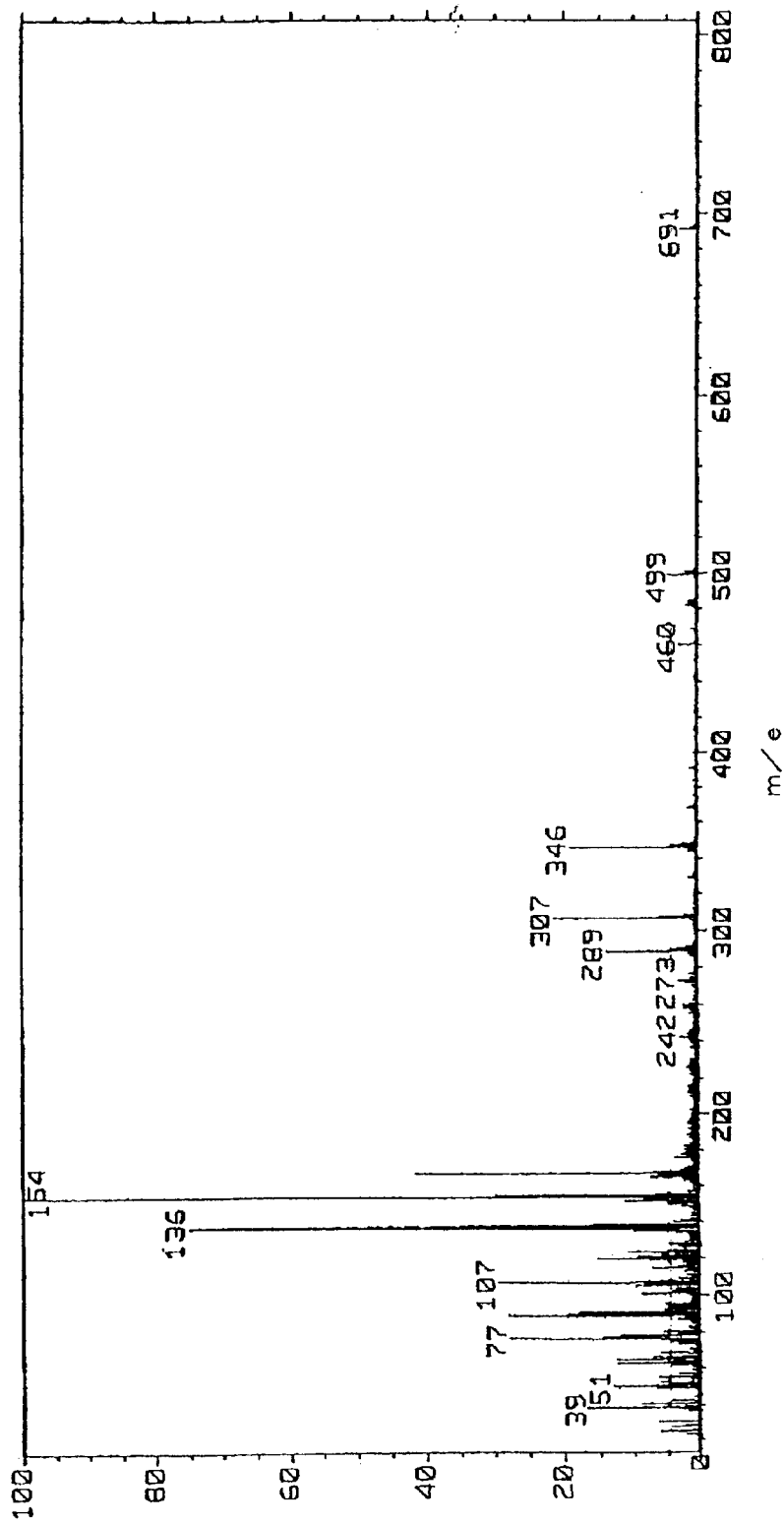
FIG. 6 is a graph showing the results of measurement by fast atom bombardment mass spectrometry of the N-sulfonyloxyimide compound (PAG2) obtained in Synthesis Example 2.

The PAG2 was also put to $^1$H-NMR analysis, infrared absorption spectrometry and fast atom bombardment mass spectrometry (M+H$^+$=346) to obtain measurement results shown in FIGS. 4, 5 and 6, respectively.

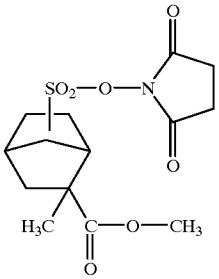
(11)

Synthesis of Acid-cleavable Group-containing Resin (B)

Synthesis Example 3

101 g of p-acetoxystyrene, 5 g of styrene, 42 g of p-t-butoxystyrene, 6 g of AIBN and 1 g of t-dodecyl mercaptan were dissolved in 160 g of propylene glycol monomethyl ether, and then polymerization was carried out for 16 hours in an atmosphere of nitrogen and at a reaction temperature kept at 70° C. After the polymerization was completed, the reaction solution was dropwise added in a large quantity of hexane, and the resin formed was solidified and purified. Next, to the resin thus purified, propylene glycol monomethyl ether was again added in an amount of 150 g, and thereafter 300 g of methanol, 80 g of triethylamine and 15 g of water were further added to effect hydrolysis reaction for 8 hours under ref lux at the boiling point. After the reaction was completed, the solvent and triethylamine were evaporated off under reduced pressure. The resultant resin was dissolved in acetone, and then dropwise added in a large quantity of water to cause to solidify. The white powder thus formed was filtered, followed by drying overnight at 50° C. under reduced pressure.

The resin thus obtained had Mw of 16,000 and Mw/Mn of 1.7, and its $^{13}$C-NMR analysis revealed that p-hydroxystyrene, styrene and p-t-butoxystyrene were in a copolymerization molar ratio of 72:5:23. This resin is designated as resin (B-1).

The Mw and Mn of the resin (B-1) and resins obtained in Synthesis Examples 4 to 13 were measured by gel permeation chromatography (GPC) with monodisperse polystyrene as a standard, using GPC columns available from Toso Co. Ltd. (two columns of G2000H$_{XL}$, one column of G3000H$_{XL}$, and one column of G4000H$_{XL}$) under analysis conditions of a flow rate of 1.0 ml/minute, eluting-solvent tetrahydrofuran and a column temperature of 40° C.

Synthesis Example 4

100 g of p-acetoxystyrene, 25 g of t-butyl acrylate, 18 g of styrene, 6 g of AIBN and 1 g of t-dodecyl mercaptan were dissolved in 230 g of propylene glycol monomethyl ether, and then polymerization was carried out for 16 hours in an atmosphere of nitrogen and at a reaction temperature kept at 70° C. After the polymerization was completed, the reaction solution was dropwise added in a large quantity of hexane, and the resin formed was solidified and purified. Next, to the resin thus purified, propylene glycol monomethyl ether was again added in an amount of 150 g, and thereafter 300 g of methanol, 80 g of triethylamine and 15 g of water were further added to effect hydrolysis reaction for 8 hours under reflux at the boiling point. After the reaction was completed, the solvent and triethylamine were evaporated off under reduced pressure. The resultant resin was dissolved in acetone, and then dropwise added in a large quantity of water to cause to solidify. The white powder thus formed was filtered, followed by drying overnight at 50° C. under reduced pressure.

The resin thus obtained had Mw of 11,500 and Mw/Mn of 1.6, and its $^{13}$C-NMR analysis revealed that p-hydroxystyrene, t-butyl acrylate and styrene were in a copolymerization molar ratio of 61:19:20. This resin is designated as resin (B-2).

Synthesis Example 5

125 g of p-acetoxystyrene, 20 g of t-butyl acrylate, 10 g of styrene, 8 g of 2,5-dimethylhexane-2,5-diacrylate, 8 g of AIBN and 6 g of t-dodecyl mercaptan were dissolved in 170 g of propylene glycol monomethyl ether, and then polymerization was carried out for 16 hours in an atmosphere of nitrogen and at a reaction temperature kept at 70° C. After the polymerization was completed, the reaction solution was dropwise added in a large quantity of hexane, and the resin formed was solidified and purified. Next, to the resin thus purified, propylene glycol monomethyl ether was again added in an amount of 150 g, and thereafter 300 g of methanol, 80 g of triethylamine and 15 g of water were further added to effect hydrolysis reaction for 8 hours under reflux at the boiling point. After the reaction was completed, the solvent and triethylamine were evaporated off under reduced pressure. The resultant resin was dissolved in acetone, and then dropwise added in a large quantity of water to cause to solidify. The white powder thus formed was filtered, followed by drying overnight at 50° C. under reduced pressure.

The resin thus obtained had Mw of 40,000 and Mw/Mn of 2.6, and its $^{13}$C-NMR analysis revealed that p-hydroxystyrene, t-butyl acrylate, styrene and 2,5-dimethylhexane-2,5-diacrylate were in a copolymerization molar ratio of 72:10:15:3. This resin is designated as resin (B-3).

Synthesis Example 6

140 g of p-acetoxystyrene, 50 g of p-t-butoxystyrene, 9 g of 2,5-dimethylhexane-2,5-diacrylate, 8 g of AIBN and 6 g of t-dodecyl mercaptan were dissolved in 240 g of propylene glycol monomethyl ether, and then polymerization was carried out for 16 hours in an atmosphere of nitrogen and at a reaction temperature kept at 70° C. After the polymerization was completed, the reaction solution was dropwise added in a large quantity of hexane, and the resin formed was solidified and purified. Next, to the resin thus purified, propylene glycol monomethyl ether was again added in an amount of 150 g, and thereafter 300 g of methanol, 100 g of triethylamine and 15 g of water were further added to effect hydrolysis reaction for 8 hours under reflux at the boiling point. After the reaction was completed, the solvent and triethylamine were evaporated off under reduced pressure. The resultant resin was dissolved in acetone, and then dropwise added in a large quantity of water to cause to solidify. The white powder thus formed was filtered, followed by drying overnight at 50° C. under reduced pressure.

The resin thus obtained had Mw of 40,000 and Mw/Mn of 2.6, and its $^{13}$C-NMR analysis revealed that p-hydroxystyrene, p-t-butoxystyrene, and 2,5-dimethylhexane-2,5-diacrylate were in a copolymerization molar ratio of 67:30:3. This resin is designated as resin (B-4).

Synthesis Example 7

176 g of p-t-butoxystyrene was subjected to anionic polymerization in 500 ml of tetrahydrofuran at −78° C. in the presence of s-butyl lithium as a catalyst. After the polymerization was completed, the reaction solution was solidified in methanol to obtain 150 g of white poly(p-t-butoxystyrene). Thereafter, this poly(p-t-butoxystyrene) was dissolved in 600 a of dioxane, and dilute hydrochloric acid was added to effect hydrolysis reaction at 70° C. for 2 hours. Then, the reaction product formed was solidified in a large quantity of water to obtain a whites resin. Thereafter, this resin was dissolve in acetone and solidified in a large quantity of water, and this procedure was repeated. Then, the white powder thus formed was filtered, followed by drying overnight at 50° C. under reduced pressure.

The resin thus obtained had Mw of 10,400 and Mw/Mn of 1.01, and its $^{13}$C-NMR analysis revealed that it had a structure wherein only part of t-butyl groups in the poly(p-t-butoxystyrene) had been hydrolyzed, and p-t-butoxystyrene and p-t-hydroxystyrene were in a copolymerization molar ratio of 68:32. This resin is designated as resin (B-5).

Synthesis Example 8

To a solution prepared by dissolving 12 g of poly(p-hydroxystyrene) and 5 g of triethylamine in 50 g of dioxane, 7 g of di-t-butyl carbonate was added with stirring, and then stirred at room temperature for 6 hours, followed by addition of oxalic acid to neutralize the triethylamine. Thereafter, the reaction solution was dropwise added in a large quantity of water to cause the resin to solidify. The resin thus solidified was washed with pure water several times, followed by filtration and then drying overnight at 50° C. under reduced pressure.

The resin thus obtained had Mw of 9,200 and Mw/Mn of 1.8, and its $^{13}$C-NMR analysis revealed that it had a structure wherein 30 mole % of hydrogen atoms of phenolic hydroxyl groups in the poly(p-hydroxystyrene) had been substituted with t-butoxycarbonyl groups. This resin is designated as resin (B-6).

Synthesis Example 9

176 g of p-t-butoxystyrene was subjected to anionic polymerization in 500 ml of tetrahydrofuran at −78° C. in the presence of s-butyl lithium as a catalyst. After the polymerization was completed, the reaction solution was solidified in methanol to obtain 150 g of white poly(p-t-butoxystyrene). Thereafter, this poly(p-t-butoxystyrene) was dissolved in 600 g of dioxane, and dilute hydrochloric acid was added to effect hydrolysis reaction at 70° C. for 12 hours. Then, the reaction solution formed was solidified in a large quantity of water to obtain a white resin. Thereafter, this resin was dissolve in acetone and solidified in a large quantity of water, and this procedure was repeated. Then, the white powder thus formed was filtered, followed by drying overnight at 50° C. under reduced pressure.

The resin thus obtained was poly(p-hydroxystyrene) having Mw of 11,400 and Mw/Mn of 1.01.

Next, 24 g of this poly(p-hydroxystyrene) was dissolved in 100 g of n-butyl acetate, and the solution formed was bubbled with nitrogen gas for 30 minutes. Then, 8 g of cyclohexyl vinyl ether was added and 1 g of pyridinium p-toluenesulfonate as a catalyst was added to carry out reaction at room temperature for 12 hours. Thereafter, the reaction solution was dropwise added in an aqueous 1% by weight ammonia solution to cause the resin to precipitate, followed by filtration and then drying overnight in a 50° C. vacuum dryer.

The resin thus obtained had Mw of 13,000 and Mw/Mn of 1.01, and its $^{13}$C-NMR analysis revealed that it had a structure wherein 23 mole % of hydrogen atoms of phenolic hydroxyl groups in the poly(p-hydroxystyrene) had been substituted with 1-cyclohexyloxyethyl groups. This resin is designated as resin (B-7).

Synthesis Example 10

24 g of poly(p-hydroxystyrene) having Mw of 12,000 was dissolved in 100 g of dioxane, and the solution formed was bubbled with nitrogen gas for 30 minutes. Then, 3 g of ethyl vinyl ether, 3 g of ethyl-1-propenyl ether and 1 g of pyridinium p-toluenesulfonate as a catalyst were added to carry out reaction at room temperature for 12 hours. Thereafter, the reaction solution was dropwise added in an aqueous 1% by weight ammonia solution to cause the resin to precipitate, followed by filtration and then drying overnight in a 50° C. vacuum dryer.

The resin thus obtained had Mw of 15,000 and Mw/Mn of 1.6, and its $^{13}$C-NMR analysis revealed that it had a structure wherein 20 mole % of hydrogen atoms of phenolic hydroxyl groups in the poly(p-hydroxystyrene) had been substituted with 1-ethoxyethyl groups and 15 mole % had been substituted with 1-ethoxypropyl groups. This resin is designated as resin (B-8).

Synthesis Example 11

To a solution prepared by dissolving 120 g of poly(p-hydroxystyrene) with Mw of 12,000 and 15 g of triethylamine in 500 g of dioxane, 20 g of di-t-butyl carbonate was added with stirring, and then stirred at room temperature for further 6 hours, followed by addition of oxalic acid to neutralize the triethylamine. Thereafter, the reaction solution was dropwise added in a large quantity of water to cause the resin to solidify. The resin thus solidified was washed with pure water several times, followed by filtration and then drying overnight in a 50° C. vacuum dryer.

The resin thus obtained had Mw of 8,900 and Mw/Mn of 2.8, and its $^{13}$C-NMR analysis revealed that it had a structure wherein 9 mole % of hydrogen atoms of phenolic hydroxyl groups in the poly(p-hydroxystyrene) had been substituted with t-butoxycarbonyl groups.

Next, this resin was dissolved in 100 g of dioxane, and the solution formed was bubbled with nitrogen gas for 30 minutes. Then, 2 g of ethyl vinyl ether, 2 g of ethyl-1-propenyl ether and 1 g of pyridinium p-toluenesulfonate as a catalyst were added to carry out reaction at room temperature for 12 hours. Thereafter, the reaction solution was dropwise added in an aqueous 1% by weight ammonia solution to cause the resin to precipitate, followed by filtration and then drying overnight in a 50° C. vacuum dryer.

The resin thus obtained had Mw of 11,000 and Mw/Mn of 2.8, and its $^{13}$C-NMR analysis revealed that it had a structure wherein 14 mole % of hydrogen atoms of phenolic hydroxyl groups in the poly(p-hydroxystyrene) had been substituted with 1-ethoxyethyl groups, 11 mole % had been substituted with 1-ethoxypropyl groups and 9 mole % had been substituted with 1-butoxycarbonyl groups. This resin is designated as resin (B-9).

Synthesis Example 12

25 g of a copolymerization product of p-hydroxystyrene and p-t-butoxystyrene in a molar ratio of 90:10 was dissolved in 100 g of n-butyl acetate, and the solution formed was bubbled with nitrogen gas for 30 minutes. Then, 3.3 g of ethyl vinyl ether was added, and 1 g of pyridinium p-toluenesulfonate as a catalyst was added to carry out reaction at room temperature for 12 hours. Thereafter, the reaction solution was dropwise added in an aqueous 1% by weight ammonia solution to cause the resin to precipitate, followed by filtration and then drying overnight in a 50° C. vacuum dryer.

The resin thus obtained had Mw of 13,000 and Mw/Mn of 1.01, and its $^{13}$C-NMR analysis revealed that it had a structure wherein 23 mole % of hydrogen atoms of phenolic hydroxyl groups in the poly(p-hydroxystyrene) had been substituted with ethoxyethyl groups and 10 mole % had been substituted with t-butyl groups. This resin is designated as resin (B-10).

Synthesis Example 13

114 g of p-acetoxystyrene, 19 g of t-butyl acrylate, 32 g of p-t-butylstyrene, 6 g of AIBN and 1 g of t-dodecyl mercaptan were dissolved in 230 g of propylene glycol monomethyl ether, and then polymerization was carried out for 16 hours in an atmosphere of nitrogen and at a reaction temperature kept at 70° C. After the polymerization was completed, the reaction solution was dropwise added in a large quantity of hexane, and the resin formed was solidified and purified. Next, to the resin thus purified, propylene glycol monomethyl ether was again added in an amount of 150 g, and thereafter 300 g of methanol, 80 g of triethylamine and 15 g of water were further added to effect hydrolysis reaction for 8 hours under reflux at the boiling point. After the reaction was completed, the solvent and triethylamine were evaporated off under reduced pressure. The resultant resin was dissolved in acetone, and then dropwise added in a large quantity of water to cause to solidify. The white powder thus formed was filtered, followed by drying overnight at 50° C. under reduced pressure.

The resin thus obtained had Mw of 11,500 and Mw/Mn of 1.6, and its $^{13}$C-NMR analysis revealed that p-hydroxystyrene, t-butyl acrylate and p-t-butoxystyrene were in a copolymerization molar ratio of 65:15:20. This resin is designated as resin (B-11).

Chemically Amplified Positive Radiation-sensitive Resin Composition

Examples 1 to 20 & Comparative Examples 1 to 4

Ingredients shown in Tables 1 and 2 ("pbw" stands for part(s) by weight) were mixed to form uniform solutions, which were then each filtered with a membrane filter of 0.2 μm in pore size, thus composition solutions were prepared. Thereafter, the composition solutions were spin-coated on silicon wafers, and PB was carried out under conditions shown in Table 3 to form resist films with a layer thickness of 0.5 μm.

Next, in Examples 1 to 17 and Comparative Examples 1 to 4, exposure was carried out under conditions shown in Table 3, by means of a stepper NSR2205 EX12B (numerical aperture: 0.55), manufactured by Nikon K. K., and in Examples 18 to 20 by means of a unit obtained by remodeling a direct-drawing electron radiations drawing unit HL700 (accelerating voltage: 30 keV), manufactured by Hitachi Ltd., to have an accelerating voltage of 50 keV. Then, PEB was carried out under conditions shown in Table 3. Thereafter, using an aqueous 2.38% by weight tetramethylammonium hydroxide solution, the resists formed were developed by paddling at 23° C. for 1 minute, followed by washing with pure water and then drying to form resist patterns. Results of evaluation on each resist are shown in Table 4.

TABLE 1

| | Acid-generating agent (pbw) | Resin (pbw) | Additive (pbw) | Acid diffusion control agent (pbw) | Solvent (pbw) |
|---|---|---|---|---|---|
| Example 1 | PAG1(4) | a-1(2) a-3(2) | B-1(100) | F-3 (0.1) | E-4(0.2) | G-1(500) |
| Example 2 | PAG1(3) | a-4(4) | B-1(100) | | E-5 (0.15) | G-1(500) |
| Example 3 | PAG1(6) | a-1(2) a-3(0.5) | B-11(95) C-1(5) | | E-5(0.2) | G-1(500) |
| Example 4 | PAG2(4) | a-1(2) a-3(2) | B-1(100) | F-3 (0.1) | E-4(0.2) | G-1(500) |
| Example 5 | PAG2(3) | a-4(6) | B-1(100) | | E-5(0.2) | G-1(500) |
| Example 6 | PAG2(6) | a-4(2) | B-2(90) C-1(10) | | E-5(0.2) | G-1(350) G-3(150) |
| Example 7 | PAG2(6) | a-4(2) | B-3(100) | | E-5(0.2) | G-1(350) G-3(150) |
| Example 8 | PAG2(2) | a-4(6) A-2(2) | B-4(80) C-2(20) | F-3 (0.1) | E-2(0.2) | G-1(350) G-3(150) |
| Example 9 | PAG2(5) | a-3(4) | B-5(100) | | E-5(0.1) | G-1(500) |
| Example 10 | PAG2(6) | | B-6(100) | | E-5(0.1) | G-1(500) |
| Example 11 | PAG2(7) | a-5(1) | B-7(90) C-1(10) | | E-2(0.2) | G-1(350) G-2(150) |
| Example 12 | PAG2(7) | a-5(1) | B-8(90) C-1(10) | F-3 (0.2) | E-1(0.2) | G-1(350) G-2(150) |
| Example 13 | PAG2(7) | | B-9(100) | F-3 (0.2) | E-1(0.1) | G-1(350) G-2(150) |
| Example 14 | PAG2(4) | a-6(3) | B-10(80) C-2(20) | F-3 (0.2) | E-1(0.1) E-2(0.1) | G-1(350) G-2(150) |
| Example 15 | PAG2(6) | A-1(2) a-3(0.5) | B-11(95) C-1(5) | | E-5(0.2) | G-1(500) |
| Example 16 | PAG2(3) | a-5(4) | B-1(100) | | E-5(0.2) | G-1(500) |
| Example 17 | PAG1(3) | a-4(4) | B-1(100) | | E-5 (0.15) | G-1(500) |
| Example 18 | PAG1(7) | a-6(5) a-6(2) | B-1(100) | F-2(5) | E-5(0.1) | G-1(500) |
| Example 19 | PAG2(7) | | B-1(100) | | E-5(0.1) | G-1(500) |
| Example 20 | PAG2(4) | a-6(5) | B-1(100) | | E-5(0.1) | G-1(500) |

TABLE 2

| | Acid-generating agent (pbw) | Resin (pbw) | Additive (pbw) | Acid diffusion control agent (pbw) | Solvent (pbw) |
|---|---|---|---|---|---|
| Comparative Example 1 | a-1(2) a-3(2) | B-1(100) | F-3(0.1) | E-4(0.2) | G-1(500) |
| Comparative Example 2 | a-3(8) | B-1(100) | | E-5(0.2) | G-1(500) |
| Comparative Example 3 | a-4(6) a-1(2) a-3(0.5) | B-11(95) C-1(5) | | E-5(0.2) | G-1(500) |
| Comparative Example 4 | a-7(3) a-4(4) | B-1(100) | | E-5(0.15) | G-1(500) |

TABLE 3

| | PB | | | PEB | |
|---|---|---|---|---|---|
| | Temperature (° C.) | Time (S) | Exposure light source | Temperature (° C.) | Time (S) |
| Example 1 | 130 | 60 | KrF excimer laser | 130 | 60 |
| Example 2 | 130 | 60 | KrF excimer laser | 130 | 60 |
| Example 3 | 130 | 60 | KrF excimer laser | 130 | 60 |
| Example 4 | 130 | 60 | KrF excimer laser | 130 | 60 |
| Example 5 | 130 | 60 | KrF excimer laser | 130 | 60 |
| Example 6 | 110 | 60 | KrF excimer laser | 130 | 60 |
| Example 7 | 110 | 60 | KrF excimer laser | 130 | 60 |
| Example 8 | 130 | 60 | KrF excimer laser | 130 | 60 |
| Example 9 | 110 | 60 | KrF excimer laser | 100 | 60 |
| Example 10 | 90 | 60 | KrF excimer laser | 100 | 60 |
| Example 11 | 90 | 60 | KrF excimer laser | 100 | 60 |
| Example 12 | 90 | 60 | KrF excimer laser | 100 | 60 |
| Example 13 | 90 | 60 | KrF excimer laser | 100 | 60 |

TABLE 3-continued

|  | PB | | | PEB | |
|---|---|---|---|---|---|
|  | Temperature (° C.) | Time (S) | Exposure light source | Temperature (° C.) | Time (S) |
| Example 14 | 90 | 60 | KrF excimer laser | 100 | 60 |
| Example 15 | 130 | 60 | KrF excimer laser | 130 | 60 |
| Example 16 | 130 | 60 | KrF excimer laser | 130 | 60 |
| Example 17 | 130 | 60 | KrF excimer laser | 130 | 60 |
| Example 18 | 110 | 60 | Electron radiation | 130 | 60 |
| Example 19 | 110 | 60 | Electron radiation | 130 | 60 |
| Example 20 | 110 | 60 | Electron radiation | 130 | 60 |
| Comparative Example 1 | 130 | 60 | KrF excimer laser | 130 | 60 |
| Comparative Example 2 | 130 | 60 | KrF excimer laser | 130 | 60 |
| Comparative Example 3 | 130 | 60 | KrF excimer laser | 130 | 60 |
| Comparative Example 4 | 130 | 60 | KrF excimer laser | 130 | 60 |

TABLE 4

|  | Sensitivity (mJ/cm$^2$) | Resolution (μm) | Pattern shape | Development defects | Storage stability |
|---|---|---|---|---|---|
| Example 1 | 25 | 0.20 | good | good | good |
| Example 2 | 22 | 0.21 | good | good | good |
| Example 3 | 24 | 0.19 | good | good | good |
| Example 4 | 23 | 0.18 | good | good | good |
| Example 5 | 23 | 0.17 | good | good | good |
| Example 6 | 25 | 0.19 | good | good | good |
| Example 7 | 24 | 0.20 | good | good | good |
| Example 8 | 24 | 0.20 | good | good | good |
| Example 9 | 23 | 0.20 | good | good | good |
| Example 10 | 26 | 0.20 | good | good | good |
| Example 11 | 23 | 0.20 | good | good | good |
| Example 12 | 22 | 0.20 | good | good | good |
| Example 13 | 22 | 0.18 | good | good | good |
| Example 14 | 23 | 0.20 | good | good | good |
| Example 15 | 25 | 0.18 | good | good | good |
| Example 16 | 25 | 0.19 | good | good | good |
| Example 17 | 24 | 0.17 | good | good | good |
| Example 18 | 4uC | 0.17 | good | good | good |
| Example 19 | 3uC | 0.17 | good | good | good |
| Example 20 | 3uC | 0.18 | good | good | good |
| Comparative Example 1 | 34 | 0.22 | good | poor | good |
| Comparative Example 2 | 27 | 0.22 | poor | good | good |
| Comparative Example 3 | 26 | 0.22 | poor | good | poor |
| Comparative Example 4 | 26 | 0.22 | good | good | poor |

Chemically Amplified Negative Radiation-sensitive Resin Composition

Examples 21 to 23 & Comparative Example 5

Ingredients shown in Table 5 ("pbw" stands for part(s) by weight) were mixed to form uniform solutions, which were then each filtered with a membrane filter of 0.2 μm in pore size, thus composition solutions were prepared. Thereafter, the composition solutions were spin-coated on silicon wafers, and PB was carried out under conditions shown in Table 6 to form resist films with a layer thickness of 0.5μm.

Next, exposure was carried out under conditions shown in Table 6, by means of a stepper NSR2205 EX12B (numerical aperture: 0.55), manufactured by Nikon K.K., and then PEB was carried out under conditions shown in Table 6. Thereafter, using an aqueous 2.38% by weight tetramethylammonium hydroxide solution, the resists formed were developed by paddling at 23° C. for 1 minute, followed by washing with pure water and then drying to form resist patterns. Results of evaluation on each resist are shown in Table 7.

TABLE 5

|  | Acid-generating agent (pbw) | | Resin (pbw) | Additive cross-linking agent (pbw) | Acid diffusion control agent (pbw) | Solvent (pbw) |
|---|---|---|---|---|---|---|
| Example 21 | PAG1(1) | a-6(2) | c-2 (100) | D-1(7) | E-1(0.5) | E-1(600) |
| Example 22 | PAG2(1) | a-6(2) | c-1 (100) | D-2(7) | E-1(0.5) | E-1(600) |
| Example 23 | PAG2(1) | a-6(2) | c-2 (100) | D-2(7) | E-1(0.5) | E-1(600) |
| Comparative Example 5 | a-6(3) | | c-2 (100) | D-1(7) | E-1(0.5) | E-1(600) |

TABLE 6

| | PB | | | PEB | |
|---|---|---|---|---|---|
| | Temperature (° C.) | Time (S) | Exposure light source | Temperature (° C.) | Time (S) |
| Example 21 | 90 | 60 | KrF excimer laser | 110 | 60 |
| Example 22 | 90 | 60 | KrF excimer laser | 110 | 60 |
| Example 23 | 90 | 60 | KrF excimer laser | 110 | 60 |
| Comparative Example 5 | 90 | 60 | KrF excimer laser | 110 | 60 |

TABLE 7

| | Sensitivity (mJ/cm$^2$) | Resolution (μm) | Pattern shape | Development defects | Storage stability |
|---|---|---|---|---|---|
| Example 21 | 30 | 0.20 | good | good | good |
| Example 22 | 29 | 0.20 | good | good | good |
| Example 23 | 29 | 0.20 | good | good | good |
| Comparative Example 5 | 30 | 0.21 | poor | good | good |

Here, the evaluation of resists was made in the following way.

Sensitivity:

The resist film formed on the silicon wafer was subjected to exposure, immediately followed by PEB, and then alkaline development, water washing, and drying to form a resist pattern, where the amount of exposure that forms a line-and-space pattern (1L1S) of 0.22 μm in line width in a line width of 1:1 was regarded as optimum amount of exposure. Sensitivity was evaluated by this optimum amount of exposure.

Resolution:

Minimum size (μm) of a line-and-space pattern (1L1S) resolved when exposed at the optimum amount of exposure was regarded as resolution.

Pattern Shape:

In the line-and-space pattern (1L1S) of 0.22 μm, a cross section of the pattern was measured with a scanning electron microscope. Line width at the upper part of the pattern cross section is represented by La, and line width at its lower part by Lb, where a case of 0.9<La/Lb<1.1 was evaluated as "good", a case of 0.9≧La/Lb as "round top (poor)", and a case of La/Lb≧1.1 as "T-type (poor)".

Development Defects:

A case in which no development defect was seen and, in the measurement of the number of development defects by means of KLA2112 (manufactured by KLA Tencor Co), the total number of clusters and non-clusters was less than 10 was evaluated as "good"; a case in which development defects were visually seen and, in the measurement of the number of development defects by means of KLA2112, the total number of clusters and non-clusters was more than 10, as "poor".

Storage Stability:

The results of evaluation of resists formed using composition solutions stored at 23° C. for 6 month after preparation was compared with the results of evaluation of resists formed using composition solutions immediately after preparation. A case in which no change was seen in the sensitivity, resolution and pattern shape and also neither development defects were seen to have occurred nor foreign matter was seen to have appeared in composition solutions after the above storage was evaluated as "good"; and a case in which any change was seen in any one of the sensitivity, resolution and pattern shape or development defects were seen to have occurred and/or foreign matter was seen to have appeared in composition solutions after the above storage, as "poor".

In each Example and Comparative Example, the acid-generating agent (A), additional acid-generating agent, alkali-soluble resin (C), acid diffusion control agent, other additives and solvents are as shown below.

Acid-generating agent (A):
A-1: PAG1
A-2: PAG2
Additional acid-generating agent:
a-1: Bis(4-t-butylphenyl)iodonium nonafluoro-n-butane sulfonate
a-2: Bis(4-t-butylphenyl)iodonium 10-camphor sulfonate
a-3: Bis (4-t-butylphenyl) iodonium trifluoromethane sulfonate
a-4: n-Trifluoromethanesulfonyloxy-5-norbornene-2,3-dicarboxyimide
a-5: Bis(cyclohexylsulfonyl)diazomethane
a-6: Trifluorophenylsulfonium trifluoromethane sulfonate
a-7: N-(10-camphorsulfonyloxy)succinimide
Alkali-soluble resin (C):
C-1: Poly(p-hydroxystyrene) (Mw=7,500, Mw/Mn=1.1)
C-2: Hydroxystyrene/styrene copolymer (copolymerization molar ratio=8:2, Mw=4,500, Mw/Mn=11)
Acid diffusion control agent:
E-1: Tri-n-octylamine
E-2: Triethanolamine
E-3: 2-Phenylpyridine
E-4: N,N,N,N,-tetrakis(2-hydroxypropyl)ethylenediamine
E-5: 2-Phenylbenzimidazole
Other additives:
F-1: Poly(p-hydroxystyrene) (Mw=3,000)
F-2: 2,2-Bis(4-t-butoxylphenyl)propane
F-3: 1-Adamantane carboxylic acid
Cross-linking agent (D):
D-1: Dimethoxyurea (trade name: MX290; available from Sanwa Chemical Co., Ltd.)
D-2: Tetramethoxymethyl glycoluril (trade name: CYMEL1174; available from Mistui Cyanamide Co.)
Solvent:
G-1: Ethyl lactate
G-2: Ethyl 3-ethoxypropionate
G-3: Propylene glycol monomethyl ether acetate
G-4: 2-Heptanone As described above, the N-sulfonyloxyimide compound of the present invention has a structure suited for commercial-scale manufacture, especially can generate an acid in a good efficiency as having a high sensitivity (low exposure energy quantity) to far-ultraviolet radiations and charged-particle radiations, does not damage any semiconductors, has no problem of volatilization or side reaction, and can keep dark reaction from taking place or cause no impurity during the storage of resist solutions. Thus, this compound is very useful as a radiation-sensitive acid-generating agent component of radiation-sensitive resin compositions used as chemically amplified resists having a high resolution suited for fine processing.

Accordingly, the chemically amplified positive radiation-sensitive resin composition and chemically amplified negative radiation-sensitive resin composition making use of the N-sulfonyloxyimide compound of the present invention as a radiation-sensitive acid-generating agent can very preferably be used in the fabrication of semiconductor devices which are being further made finer in future and are making severer requirement-for the quality of resists.

What is claimed is:

1. An N-sulfonyloxyimide compound represented by the following general formula (1):

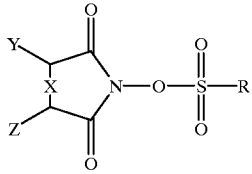
(1)

wherein X represents a single bond or a double bond, Y and Z each independently represent a hydrogen atom or a substituted or unsubstituted alkyl group having 1 to 10 carbon atoms, or Y and Z combine to form an alicyclic structure or heterocyclic structure; and R is a group represented by the following general formula (2):

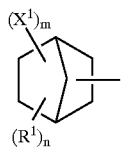
(2)

wherein $X^1$ represents an organic group having an ester linkage, having 2 to 10 carbon atoms, and, when $X^1$ is present in plurality, $X^1$'s are the same as or different from each other; $R^1$ represents an alkyl group having 1 to 10 carbon atoms or an alkoxyl group having 1 to 10 carbon atoms, and, when $R^1$ is present in plurality, $R^1$'s are the same as or different from each other; and m is an integer of 1 to 11 and n is an integer of 0 to 10, satisfying $m+n \leq 11$.

2. The N-sulfonyloxyimide compound according to claim 1, wherein the alicyclic structure or heterocyclic structure formed by combination of Y and Z is any of structures represented by the following formulas as shown as the left-half moiety of the general formula (1):

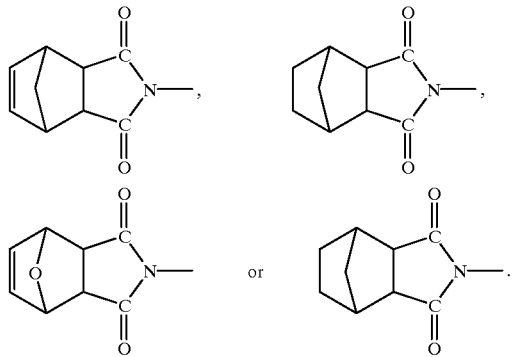

3. The N-sulfonyloxyimide compound according to claim 1, wherein the $X^1$ in the general formula (2) is a group selected from the group consisting of the groups represented by the following formulas (5-1) to (5-4):

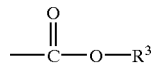
(5-1)

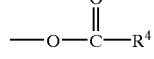
(5-2)

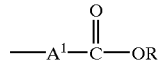
(5-3)

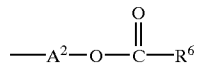
(5-4)

4. A process for producing the N-sulfonyloxyimide compound as defined in claim L, the process comprising the steps of:

subjecting a substituted or unsubstituted ethylene having the formula (4a) given below and a substituted or unsubstituted cyclopentadiene having the formula (4b) given below, at least one of the ethylene compound (4a) and the cyclopentadiene compound (4b) being a substituted compound, to the Diels-Alder reaction to thereby synthesize an alicyclic olefin compound having the formula (4c) given below, carrying out an addition reaction of the alicyclic olefin compound having the formula (4c) with a bisulfite to obtain an alicyclic sulfonic acid having the formula (4d) given below, allowing the alicyclic sulfonate having the formula (4d) to react with thionyl chloride to synthesize a sulfonyl chloride having the formula (4e) given below, allowing the thus obtained sulfonyl chloride having the formula (4e) to react with an N-hydroxyimide having the formula (4f) given below, to produce said N-sulfonyloxyimide compound

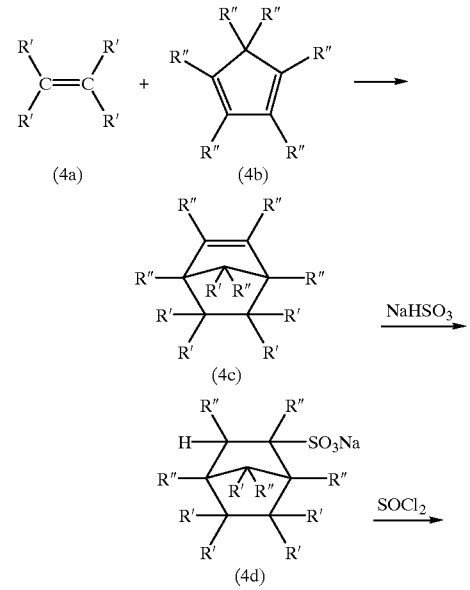

-continued

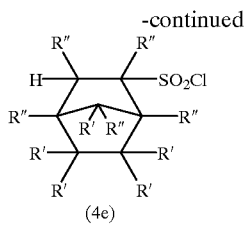

(4e)

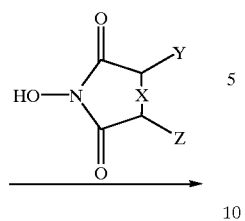

wherein in Reaction Scheme above, R"'s and R"''s each represent a hydrogen atom or the same group as $X^1$ or $R^1$ in the general formula (2) in claim 1; at least one of R"'s and at least one of R"''s each represent the same group as $X^1$ in said general formula (2); and X, Y and Z are as defined in relation to the general formula (1) in claim 1.

5. A chemically amplified positive radiation-sensitive resin composition comprising (A) a radiation-sensitive acid-generating agent of the N-sulfonyloxyimide compound as defined in claim 1, and (B) an alkali-insoluble or alkali-slightly-soluble resin protected with an acid-cleavable group. The resin being capable of turning soluble in alkali upon cleavage of the acid-cleavable group.

6. The positive radiation-sensitive resin composition according to claim 5, wherein the component-(B) protected resin is a resin formed by substituting a part or the whole of hydrogen atoms of phenolic hydroxyl groups or hydrogen atoms of carboxyl groups contained in a phenolic hydroxyl group- or carboxyl group-containing polymer or copolymer which is selected from the group consisting of a hydroxystyrene/hydroxy-α-methylstyrene copolymer, a hydroxystyrene/styrene copolymer a copolymer of hydroxystyrene with a (meth)acrylic acid, a copolymer of hydroxy-α-methylstyrene with a (meth)acrylic acid and a copolymer of hydroxystyrene and hydroxy-α-methylstyrene with a (meth)acrylic acid.

7. The positive radiation-sensitive resin composition according to claim 5, wherein the component-(B) protected resin has a weight-average molecular weight in terms of polystyrene as measured by gel permeation chromatography, of from 1,000 to 150,000.

8. The positive radiation-sensitive resin composition according to claim 5, which further comprises a radiation-sensitive acid-generating agent other than said component-(A) N-sulfonyloxyimide compound.

9. The positive radiation-sensitive resin composition according to claim 8, which comprises an onium salt compound as said other radiation-sensitive acid-generating agent.

10. The positive radiation-sensitive resin composition according to claim 5, which further comprises a nitrogen-containing organic compound as an acid diffusion control agent.

11. The positive radiation-sensitive resin composition according to claim 5, which further comprises (C) an alkali-soluble resin and/or a low-molecular weight alkali-solubility control agent having an acid-cleavable protective group.

12. A chemically amplified negative radiation-sensitive resin composition comprising (A) a radiation-sensitive acid-generating agent of the N-sulfonyloxyimide compound as defined in claim 1, (C) an alkali-soluble resin and (D) a compound capable of cross-linking the alkali-soluble resin in the presence of an acid.

13. The negative radiation-sensitive resin composition according to claim 12, wherein the component-(C) alkali-soluble resin is an addition polymerization resin having at least one of repeating units represented by the following formulas (7-1) to (7-3), or a polycondensation resin having a repeating unit represented by the following formula (7-4):

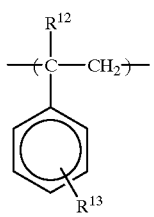
(7-1)

wherein in the formula (7-1), $R^{12}$ represents a hydrogen atom or a methyl group, $R^{13}$ represents —OH, —COOH, —$R^{14}$COOH, —O$R^{14}$OOH or —OCO$R^{14}$COOH wherein $R^{14}$ represents —(CH$_2$)$_g$, where g represents an integer of 1 to 4,

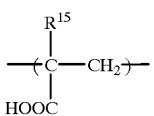
(7-2)

wherein in the formula (7-2), $R^{15}$ represents a hydrogen atom or a methyl group,

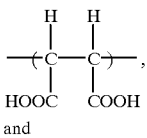
(7-3)

and

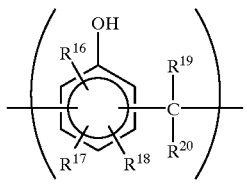
(7-4)

wherein in the formula (7-4), $R^{16}$, $R^{17}$, $R^{18}$, $R^{19}$ and $R^{20}$ each independently represent a hydrogen atom or an alkyl group having 1 to 4 carbon atoms.

14. The negative radiation-sensitive resin composition according to claim 12, wherein the component-(C) alkali-soluble resin has a weight-average molecular weight in terms of polystyrene as measured by gel permeation chromatography, of from 1,000 to 150,000.

15. The negative radiation-sensitive resin composition according to claim 12, which comprises as the component-(D) compound capable of cross-linking the alkali-soluble resin a compound having any of cross-linkable substituents represented by the following formulas (8-1) to (8-5):

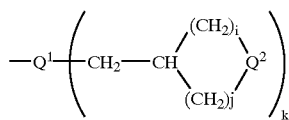

(8-1)

wherein in the formula (8-1), k is 1 or 2, $Q^1$ represents a single bond, —O—, —S—, —COO— or —NH— when k is 1, or represents a trivalent nitrogen atom when k is 2; $Q^2$ represents —O— or —S—; and i represents an integer of 0 to 3, and j an integer of 1 to 3, where i+j=1 to 4,

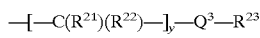

(8-2)

wherein in the formula (8-2), $Q^3$ represents —O—, —COO— or —CO—; $R^{21}$ and $R^{22}$ each independently represent a hydrogen atom or an alkyl group having 1 to 4 carbon atoms; $R^{23}$ represents an alkyl group having 1 to 5 carbon atoms, an aryl group having 6 to 12 carbon atoms or an aralkyl group having 7 to 14 carbon atoms; an y is an integer of 1 or more,

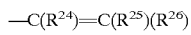

(8-3)

wherein in the formula (8-3), $R^{24}$, $R^{25}$ and $R^{26}$ each independently represent a hydrogen atom or an alkyl group having 1 to 4 carbon atoms,

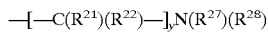

(8-4)

wherein in the formula (8-4), $R^{21}$ and $R^{22}$ have the same definition, respectively, as the $R^{21}$ and $R^{22}$ in the formula (8-2), $R^{27}$ and $R^{28}$ each independently represent a hydrogen atom or an alkyloyl group having 1 to 5 carbon atoms, and y is an integer of 1 or more,

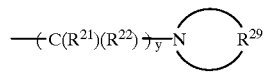

(8-5)

wherein in the formula (8-5), $R^{21}$ and $R^{22}$ have the same definition, respectively, as the $R^{21}$ and $R^{22}$ in the formula (8-2); $R^{29}$ represents a divalent organic group having a hetero atom of any of an oxygen atom, a sulfur atom and a nitrogen atom and forming a 3 to 8-membered ring; and y is an integer of 1 or more.

16. The negative radiation-sensitive resin composition according to claim 12, which further comprises a radiation-sensitive acid-generating agent other than said component-(A) N-sulfonyloxyimide compound.

17. The negative radiation-sensitive resin composition according to claim 16, which comprises an onium salt compound as said other radiation-sensitive acid-generating agent.

18. The negative radiation-sensitive resin composition according to claim 12, which further comprises a nitrogen-containing organic compound as an acid diffusion control agent.

19. The negative radiation-sensitive resin composition according to claim 12, which further comprises (B) an alkali-insoluble or alkali-slightly-soluble resin protected with an acid-cleavable group, the resin being capable of turning soluble in alkali upon cleavage of the acid-cleavable group.

20. The negative radiation-sensitive resin composition according to claim 12, wherein said the component (A) radiation-sensitive acid-generating agent is present in an amount of 0.001 to 70 parts by weight, and said the component (D) compound capable of cross-linking the alkali-soluble resin is present in an amount of 5 to 95 parts by weight, per 100 parts by weight of said component (C) alkali-soluble resin.

21. The positive radiation-sensitive resin composition according to claim 5, wherein said the component (A) radiation-sensitive acid-generating agent is present in an amount of 0.001 to 70 parts by weight per 100 parts by weight of said component (B) protected resin.

* * * * *